(12) United States Patent
Boateng

(10) Patent No.: US 12,122,771 B2
(45) Date of Patent: Oct. 22, 2024

(54) COMPOUNDS USEFUL FOR TREATMENT OF SUBSTANCE USE DISORDER

(71) Applicant: HIGH POINT UNIVERSITY, High Point, NC (US)

(72) Inventor: Comfort Ahenkan Boateng, High Point, NC (US)

(73) Assignee: High Point University, High Point, NC (US)

( * ) Notice: Subject to any disclaimer, the term of this patent is extended or adjusted under 35 U.S.C. 154(b) by 0 days.

(21) Appl. No.: 17/675,696

(22) Filed: Feb. 18, 2022

(65) Prior Publication Data

US 2022/0274978 A1 Sep. 1, 2022

Related U.S. Application Data

(60) Provisional application No. 63/151,242, filed on Feb. 19, 2021.

(51) Int. Cl.
*C07D 417/14* (2006.01)
*A61P 25/30* (2006.01)
*C07D 417/06* (2006.01)

(52) U.S. Cl.
CPC ............ *C07D 417/14* (2013.01); *A61P 25/30* (2018.01); *C07D 417/06* (2013.01)

(58) Field of Classification Search
CPC ...... C07D 471/14; C07D 471/06; A61P 25/30
See application file for complete search history.

(56) References Cited

U.S. PATENT DOCUMENTS

| 5,563,142 A * | 10/1996 | Palmer ................. C07D 491/04 514/183 |
| 2006/0172995 A1 | 8/2006 | Cowart et al. |
| 2013/0064770 A1 * | 3/2013 | Newington .......... C07D 471/04 544/182 |
| 2019/0365758 A1 * | 12/2019 | Ablordeppey .......... A61P 11/00 |

OTHER PUBLICATIONS

Zhu et al., 53 Euro. J. Med. Chem. 124-132 (2012) (CAS Abstract) (Year: 2012).*
Sampson et al., 22(12) Bioorg. & Med. Chem. 3105-3114 (2014) (CAS Abstract) (Year: 2014).*
Bergman, J., Rheingold, C.G. (2015). *Dopamine D4 receptor antagonists for the treatment of cocaine use disorders.* CNS & Neurological Disorders—Drug Targets, 14, 707-715.
Di Ciano, P., Grandy, D.K., & LeFoll, B. (2014). *Dopamine D4 receptors in psychostimulant addiction.* In Advances in Pharmacology, 69, 301-321.
Lindsley, C. W. & Hopkins, C.R. (2017). *Return of D4 dopamine receptor antagonists in drug discovery.* Journal of Medicinal Chemistry, 60(17), 7233-7243.
Sampson, D. Zhu, X. Y., Eyunni, S.V.K., Etukala, J.R., Ofori, E., Bricker, B., Lamango, N.S., Setola, V., Roth, B.L., & Ablordeppey, S.Y. (2014). *Identification of a new selective dopamine D4 receptor ligand.* Bioorganic and Medicinal Chemistry, 22, 3105-3114.
Wang, S., Wacker, D., Levit, A., Che, T., Betz, R.M., McCorvy, J.D., Venkatakrishnan, A.J., Huang, X., Dror, R.O, Shoichet, B.K., & Roth, B.L. (2017). *D4 dopamine receptor high resolution structures enable the discovery of selective agonists.* Science, 358, 381-386.

* cited by examiner

*Primary Examiner* — Timothy R Rozof
(74) *Attorney, Agent, or Firm* — Womble Bond Dickinson (US) LLP

(57) ABSTRACT

The disclosure provides compounds which exhibit dopamine receptor antagonist activity and which may be useful as therapeutic agents for the treatment of diseases and disorders associated with dopamine receptors. Also provided are methods for the preparation of such compounds, pharmaceutical compositions comprising the disclosed compounds, and methods for treating diseases or disorders with such compounds or pharmaceutical compositions.

22 Claims, 4 Drawing Sheets

| Tissue | $C_{max}$ (nmol/ml or nmol/g) | Tmax (h) | $AUC_{0-t}$ (nmol*h/ml or nmol*h/g) | $t_{1/2}$ (h) | $AUC_{Brain:Plasma}$ Ratio |
|---|---|---|---|---|---|
| Plasma | 1.45 | 0.25 | 1.05 | 0.82 | 3.5 |
| Brain | 4.52 | 0.25 | 3.67 | 1.09 | |

COMPOUNDS USEFUL FOR TREATMENT OF SUBSTANCE USE DISORDER

CROSS-REFERENCE TO RELATED APPLICATIONS

The present application claims priority and the benefit of U.S. Provisional Patent Application No. 63/151,242, filed Feb. 19, 2021, the disclosure of which is incorporated herein by reference in its entirety.

FEDERALLY SPONSORED RESEARCH OR DEVELOPMENT

This invention was made with government support under Grant R21DA050896, awarded by the National Institutes of Health. The government has certain rights in the invention.

FIELD OF THE INVENTION

The present application is directed to compounds, methods, and compositions for inhibiting certain dopamine receptors. Such compounds, methods, and compositions may find use, in particular, for treating substance use disorders caused by addiction.

BACKGROUND OF THE INVENTION

Drug addiction is a chronic relapsing disorder in which drug-taking and drug-seeking behaviors persist despite negative health and psychosocial consequences. Cocaine is the most widely used illicit psychostimulant in the United States—approximately 1.5 million people report current (i.e., past-month) cocaine use. Cocaine enhances dopaminergic signaling in the nucleus accumbens, driving drug-taking and drug-seeking behaviors. With no current FDA-approved treatment, the medication development "pipeline" for cocaine use disorder (CUD), also referred to as "cocaine addiction," requires novel therapies, evaluated in well-controlled animal studies, to develop new treatments with translational potential.

Dopamine (DA) is the major catecholamine of the central nervous system, inducing several different molecular signaling cascades when bound to one of its five known receptors. The dopamine $D_4$ receptor ($D_4R$) is a member of the $D_2$-like subfamily of dopamine receptors (including $D_2R$, $D_3R$, and $D_4R$). $D_2$-like receptors have high sequence homology and share a G-protein signaling mechanism, but differ substantially in localization within the brain and at the subcellular level. Compared to $D_2R$ and $D_3R$, $D_4Rs$ have the lowest level of brain expression and a unique distribution: $D_2R$ and $D_3R$ are localized primarily in the striatum, basal ganglia, and pituitary gland, regions associated with the effects of $D_2R$-targeting antipsychotic drugs and the motor and endocrine side-effects commonly observed with them. In contrast, $D_4Rs$ are primarily expressed in in the prefrontal cortex (PFC) and hippocampus wherein they affect attention, exploratory behavior, and performance in novel object recognition and inhibitory avoidance cognitive tasks. It is not yet clear that the optimal treatment will arise from partial agonists, full agonists or antagonists, and tests thus far have focused on $D_2R$ and $D_3R$ ligands.

While initial medications development at $D_4R$ focused on schizophrenia, $D_4R$ was ultimately not a viable target for antipsychotic drugs. However, recent studies show that $D_4R$ may be an undeveloped pharmacological target for treatment of several other neuropsychiatric disorders. Pharmacological activation of $D_4Rs$ by agonists and high-efficacy partial agonists improved cognitive performance in social recognition, novel object recognition, and 5-trial repeated acquisition inhibitory avoidance tasks, indicating an important role for $D_4R$ signaling in mediating short-term memory and cognition; thus these may be useful to treat cognitive deficits associated with schizophrenia and ADHD. $D_4R$ antagonism reduces L-DOPA-induced dyskinesias and, importantly, $D_4R$ antagonists attenuate drug-taking and -seeking behaviors in animal models of psychostimulant addiction. Notably, a recent study reported that $D_4R$ partial agonists Ro10-5824 and $D_4R$ antagonist NGD-94-1 reduced cocaine intake in monkeys (see Bergman et al., *CNS & Neurological Disorders Drug Targets* 2015, 14(6), 707-15, which is incorporated herein by reference. It would be advantageous to develop further compounds and methods for treating diseases and disorders associated with the central nervous system (CNS), e.g., cocaine addiction.

SUMMARY OF THE INVENTION

This present disclosure relates to compounds, compositions, and methods involving such compounds and compositions to treat disorders and diseases associated with the central nervous system (CNS) and, particularly, to such disorders and diseases in humans. In particular, the compounds, compositions, and methods provided herein relate to the antagonism of dopamine receptors and, as such, use of the disclosed compounds may be advantageous for treatment of a diverse array of complex pathologies, including, e.g., cognitive disorders and substance use disorders (e.g., relating to cocaine addiction).

In one aspect of the disclosure is provided a compound of Formula 1:

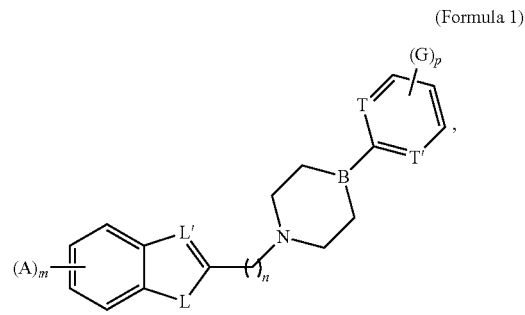

(Formula 1)

wherein:
A is selected from halogen, optionally substituted C1-6 alkyl, C1-6 alkenyl, $OR_1$, and $N(R_1)_2$;
m is an integer from 0-4 wherein, when more than one A is present, each A may be the same or different;
$R_1$ is selected from H and C1-6 alkyl;
L and L' are each independently selected from N, S, and C, so long as at least one of L and L' is N or S;
n is an integer from 1 to 6;
B is N or C;
T and T' are each independently selected from N and C; and
G is selected from halogen, C1-6 alkyl, C1-6 alkenyl, $OR_1$ and $N(R_1)_2$,
wherein, when T' is C and a substituent is present on T', it may, together with a substituent on an adjacent carbon atom, form an optionally substituted ring; and p is an integer from 0-5 wherein, when more than one G is present, each G may be the same or different.

The moieties of and substituents on compounds within the scope of Formula 1 can vary. For example, in some embodiments, L is S and L' is N. In some embodiments, n is 2-4. For example, n can be 3. In some embodiments, B is N. In other embodiments, B is C. In some embodiments, T and T' are both C. In other embodiments, T is N and T' is C. In some embodiments, m is 1 or 2.

In some embodiments, at least one A is present, and the at least one A is selected from halogen, C1-6 alkyl, and OR$_1$. For example, in some embodiments, the at least one A is selected from chloro, methyl, and methoxy. In some embodiments, m is 0. In some embodiments, p is 1 or 2. In some embodiments, at least one G is present, and the at least one G is selected from halogen, C1-6 alkyl, and OR$_1$. For example, in some embodiments, the at least one G is selected from chloro, methyl, ethyl, n-propyl, and methoxy. In some embodiments, T' is C, a first G is present on T' and a second G is present on the adjacent carbon atom, wherein the first and second G combine to form a phenyl ring. In some embodiments, p is 0.

Certain example compounds provided herein include, but are not limited to,

Compound 1

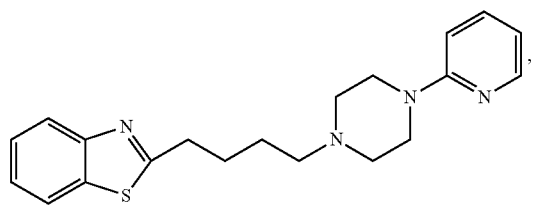

Compound 2

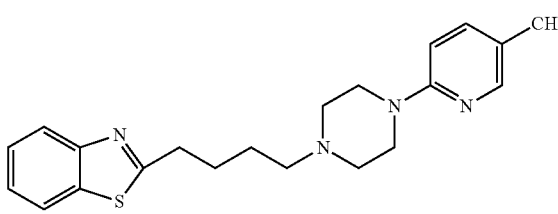

Compound 3

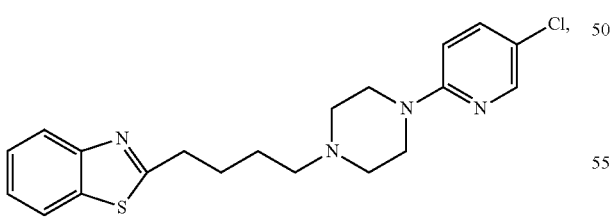

Compound 4

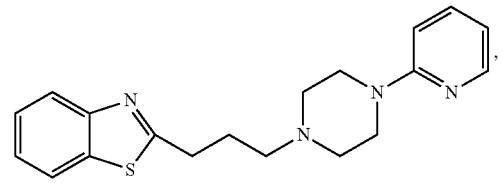

Compound 5

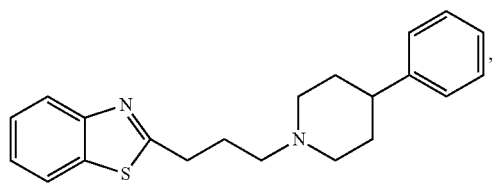

Compound 6

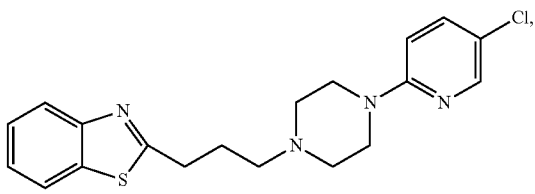

Compound 7

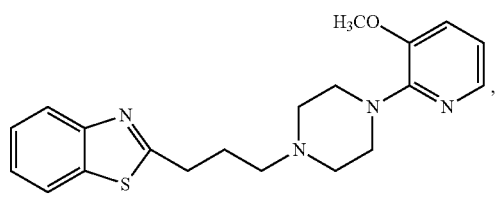

Compound 8

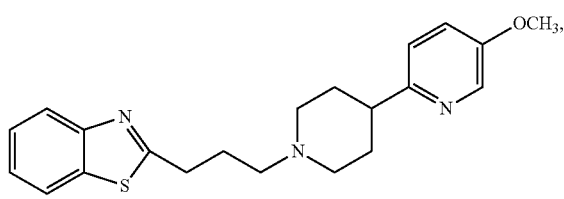

Compound 9

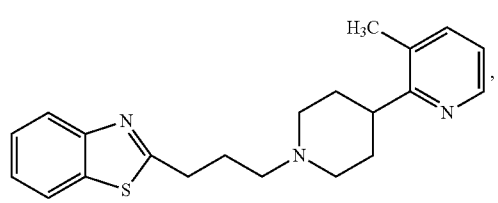

Compound 10

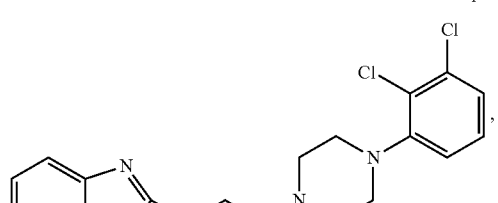

Compound 11

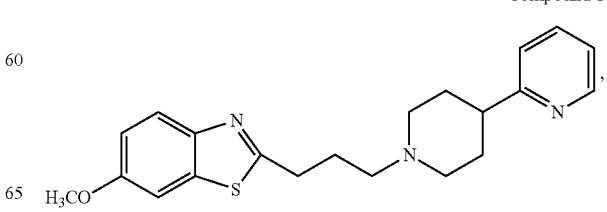

Compound 12
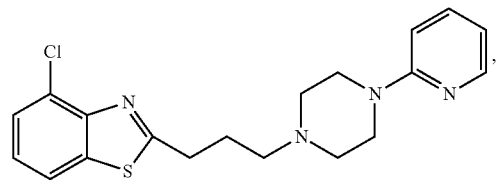
Compound 13
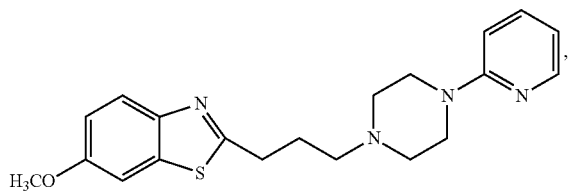
Compound 14
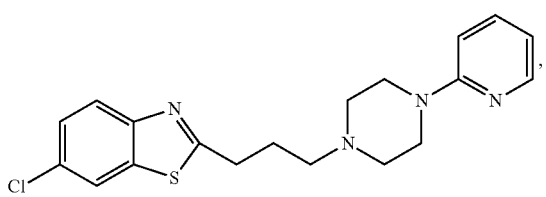
Compound 15
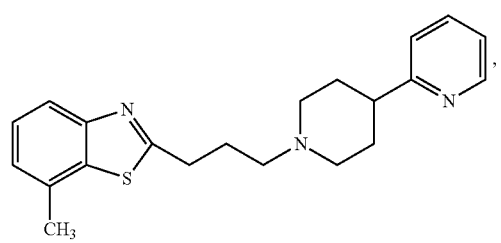
Compound 16
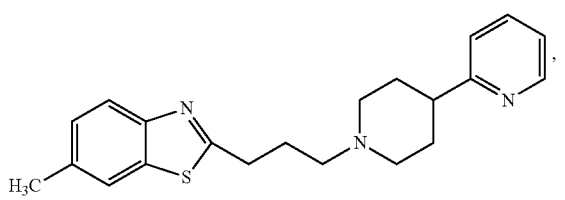
Compound 17
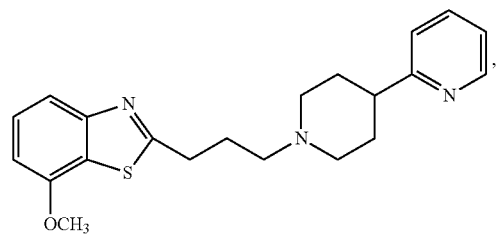
Compound 18
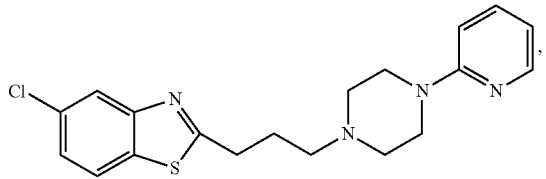
Compound 19
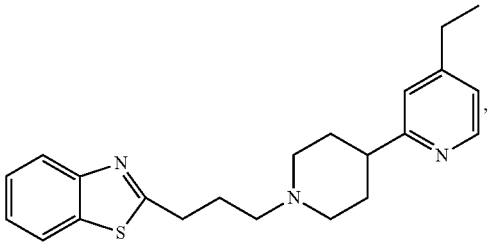
Compound 20
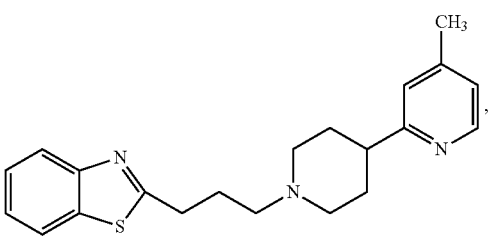
Compound 21
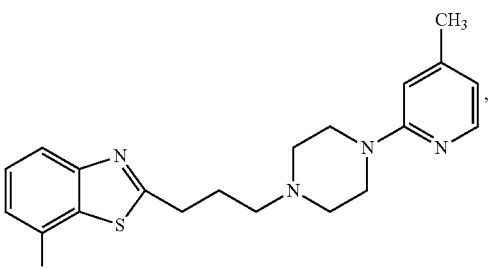
Compound 22
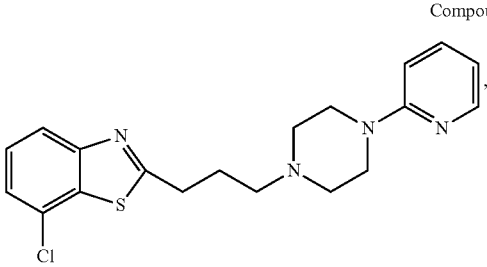
Compound 23
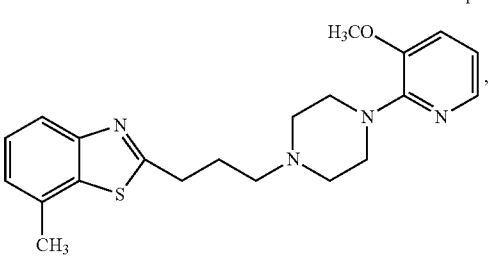
Compound 24
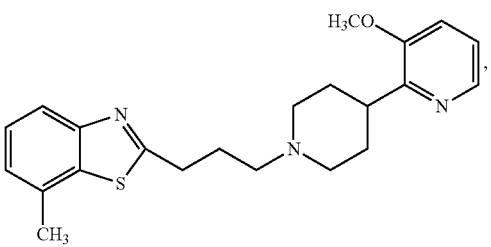

Compound 25
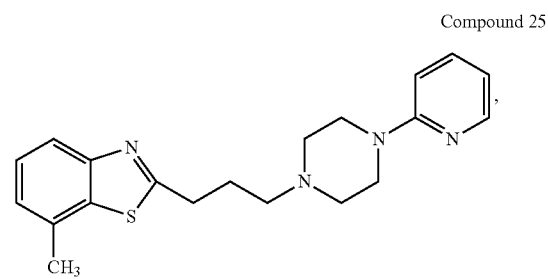
Compound 26
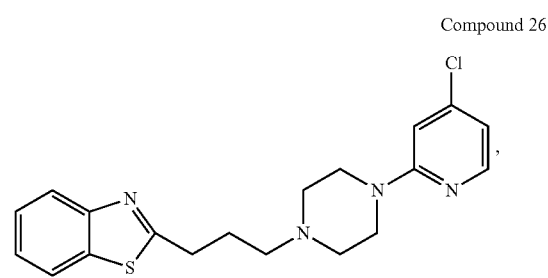
Compound 27
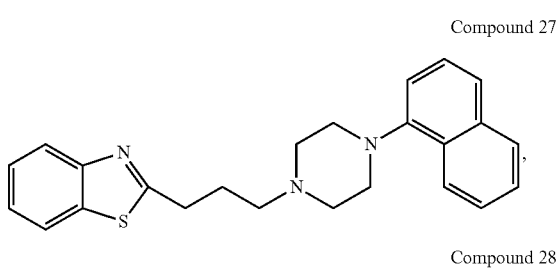
Compound 28
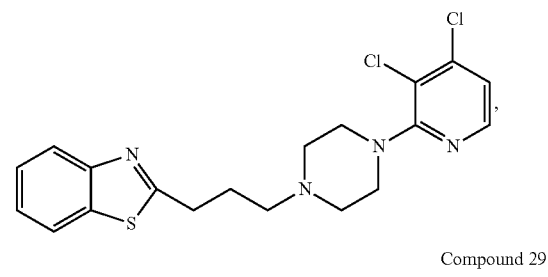
Compound 29
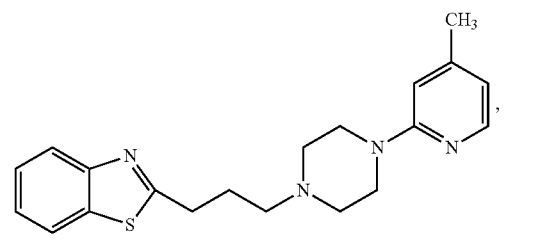
Compound 30
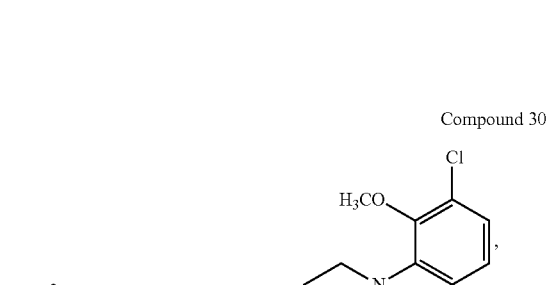
Compound 31
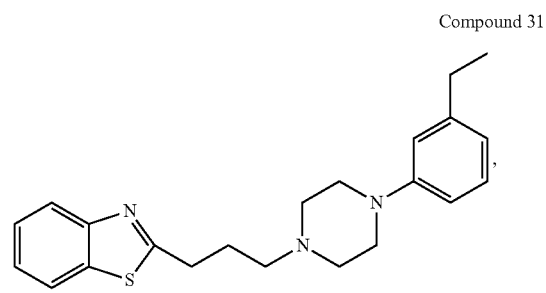
Compound 32
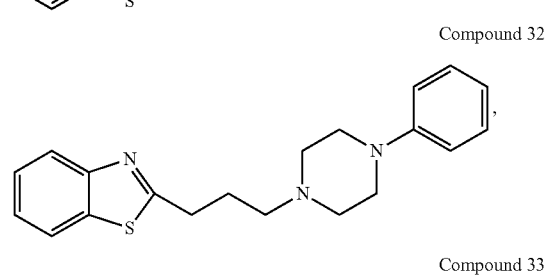
Compound 33
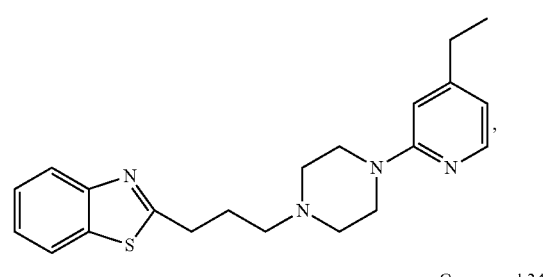
Compound 34
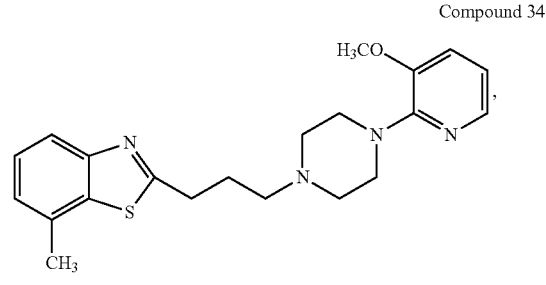
Compound 35
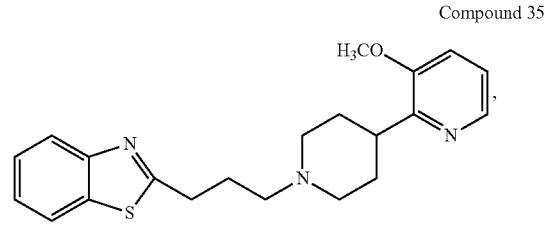
Compound 36
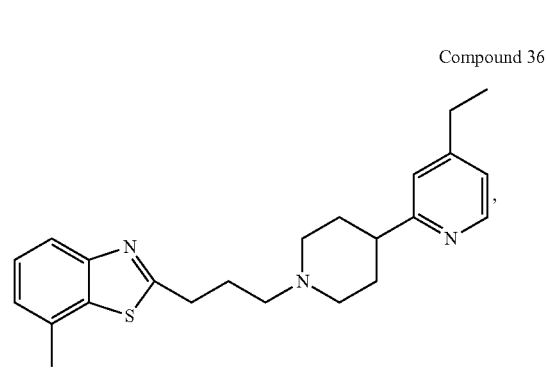

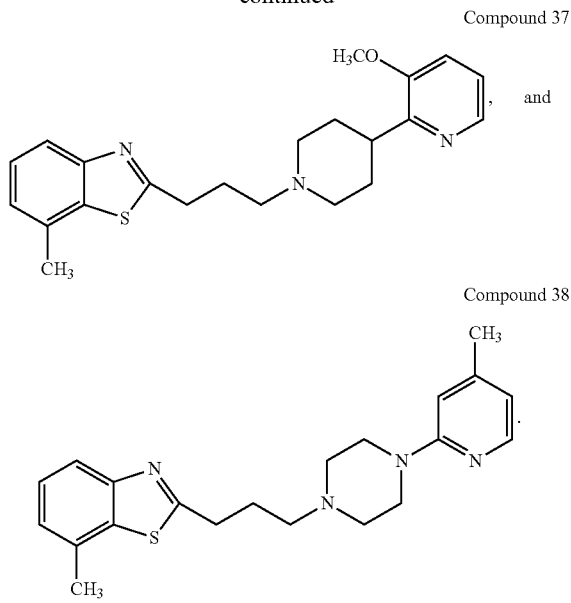

Compound 37

Compound 38

In a further aspect of the disclosure is provided a pharmaceutical composition comprising a compound as described herein and one or more pharmaceutically acceptable carriers. The compound and one or more pharmaceutically acceptable carriers can be, e.g., in the form of a mixture of components and can be formulated into various dosage forms (e.g., tablets, caplets, gels, solutions, suspensions, and the like).

The disclosure further provides a method for treating a disease or disorder associated with the central nervous system (CNS), comprising administering a therapeutically effective amount of a compound as provided herein or a pharmaceutical composition as provided herein. In some non-limiting embodiments, the disease or disorder is cocaine addiction.

These and other features, aspects and advantages of the disclosure will be apparent from a reading of the following detailed description together with the accompanying drawings, which are briefly described below. The invention includes any combination of two, three, four, or more of the above-noted embodiments as well as a combination of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

In order to provide an understanding of embodiments of the invention, reference is made to the apendix drawings, which are not necessarily drawn to scale, and in which reference to components of exemplary only and should not be construed as limiting the invention.

DETAILED DESCRIPTION

Figure 1A:
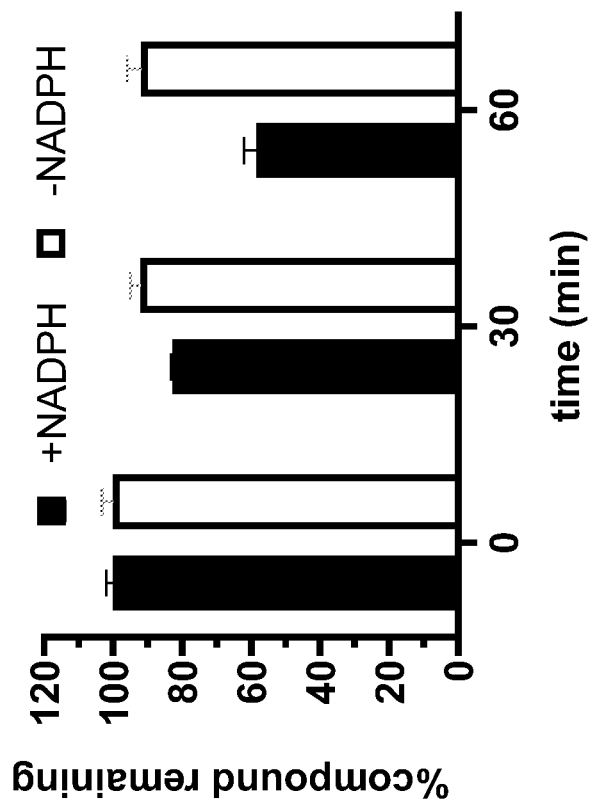
FIG. 1A and FIG. 1B are graphs of phase I metabolic stability of one example compound of an embodiment of the disclosure in rats (1A) and human (1B) liver microsomes (data expressed as mean±SEM, n=3)

The present invention now will be described more fully hereinafter. However, the invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The present disclosure provides compounds that may function as antagonists at dopamine receptors, as well as pharmaceutical compositions thereof. The disclosure also provides methods for using such compounds to treat a variety of diseases or disorders that may be responsive to the antagonism of dopamine receptors. Several lines of evidence indicate that pharmacological targeting of dopamine receptors (and, in particular, the $D_4R$ subtype) may be advantageous for a diverse array of complex pathologies, including substance use disorders and cognitive disorders. In some embodiments, the compositions and methods can be used in the treatment of addiction. Treatment can comprise the use of a compound of the present disclosure as a single active agent. In other embodiments, treatment can comprise the use of a compound of the present disclosure in combination with one or more further active agents. Specific pharmaceutical compositions and methods of treatment are further described below.

In particular, this disclosure provides compounds of the general formula:

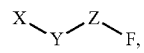

wherein:
X is an optionally substituted bicyclic heterocyclic group containing one or more nitrogen and/or or sulfur ring atoms;
Y is an optionally substituted C1-6 alkyl ("linker");
Z is an optionally substituted piperazine or piperidine; and
F is an optionally substituted aryl or heteroaryl.

The term "alkyl" as used herein means saturated straight, branched, or cyclic hydrocarbon groups (i.e., cycloalkyl groups). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "heteroalkyl" as used herein means an alkyl group, having at least one atom within the chain which is not carbon, and includes heterocycloalkyl groups. Preferred heteroatoms include sulfur, oxygen, and nitrogen.

"Optionally substituted" in reference to a substitutent group refers to substituent groups optionally substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphoric acid; phosphate; and phosphonate.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "heterocycloalkyl" means a non-aromatic, monocyclic or polycyclic ring comprising, in addition to carbon and hydrogen atoms, at least one atom within the chain which is not carbon. Preferred heteroatoms include sulfur, oxygen, and nitrogen.

The term "halo" or "halogen" as used herein means fluorine, chlorine, bromine, or iodine.

The term "alkylthio" as used herein means a thio group with one or more alkyl substituents, where alkyl is defined as above.

The term "amino" as used herein means a moiety represented by the structure $NR_2$, and includes primary amines, and secondary and tertiary amines substituted by alkyl or aryl (i.e., alkylamino or arylamino, respectively). Thus, $R_2$ may represent two hydrogen atoms, two alkyl moieties, two aryl moieties, one aryl moiety and one alkyl moiety, one hydrogen atom and one alkyl moiety, or one hydrogen atom and one aryl moiety.

The tem "cycloalkyl" means a non-aromatic, monocyclic or polycyclic ring comprising carbon and hydrogen atoms.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups include, but are not limited to, phenyl, naphthyl, tetrahydronaphthyl, and biphenyl.

In some embodiments, a compound of Formula 1 is provided wherein Y is connected to Z via a nitrogen atom on the optionally substituted piperazine or piperidine of Z.

In certain embodiments, X comprises at least one N and at least one S ring atoms. Non-limiting examples of bicyclic heterocyclic groups suitable as X in Formula 1 include, but are not limited to, indoles, benzothiophenes, purines, benzimidazoles, benzothiazoles, thiazolo[4,5-d]pyrimidine, thiazolo[4,5-d]pyridine.

In certain, non-limiting embodiments, X is a benzothiazole, i.e.:

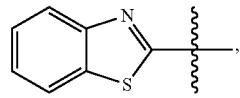

which is optionally substituted on the phenyl ring.

In certain, non-limiting embodiments, Y is an optionally substituted linear C3 alkyl (propyl), or an optionally substituted linear C4 alkyl (butyl).

In certain, non-limiting embodiments, F is optionally substituted phenyl, optionally substituted pyridine, or optionally substituted napthyl.

In certain embodiments, compounds of the following Formula 1 are provided:

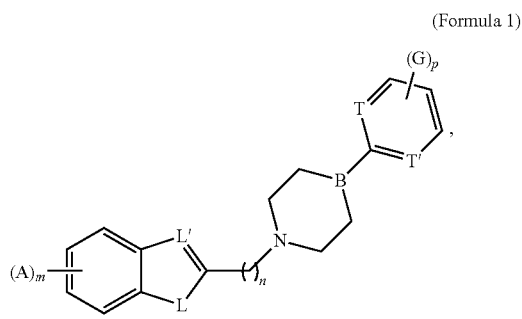

(Formula 1)

wherein:

A is as provided above with respect to the examples of substituents described with respect to the term "optionally substituted";

m is an integer from 0-4 (where, when more than one A is present, each A may be the same or different);

L and L' are each independently selected from N, S, and C, so long as at least one of L and L' is N or S;

n is an integer from 1 to 6;

B is N or C;

T and T' are each independently selected from N and C; and

G is selected from halogen, C1-6 alkyl, C1-6 alkenyl, $OR_1$, and $N(R_1)_2$; further, as shown below in Formula 1B, in certain embodiments, two adjacent G substitutents can, in some embodiments, be combined to form an optionally substituted ring (fused to the depicted phenyl or pyridinyl ring);

p is an integer from 0-5 (where, when more than one G is present, each G may be the same or different).

In some embodiments of Formula 1, T and T' are each C, such that the ring is an optionally substituted phenyl; in some embodiments, T is N and T' is C, such that the ring is an optionally substituted pyridinyl; in some embodiments, T and T' are both N, such that the ring is an optionally substituted pyrimidinyl.

In certain embodiments, L is S and L' is N, such that the compound is of Formula 1A, provided below:

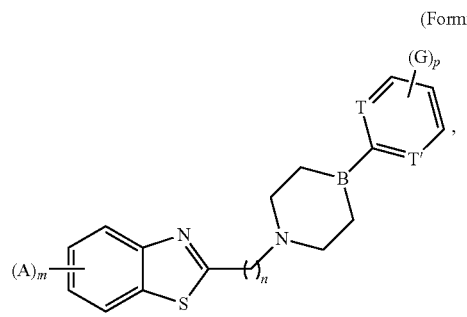

(Formula 1A)

In certain embodiments, T' in Formula 1 (and 1A) is a carbon atom, having a substituent G thereon and the adjacent carbon has a substituent G thereon, wherein such substituents form a ring, resulting in a bicyclic (fused) ring structure as shown in Formula 1B, below.

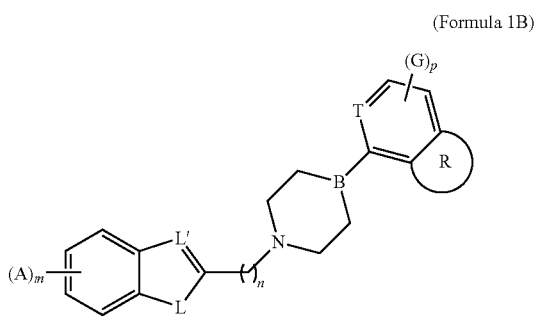

(Formula 1B)

It is understood that, in such compounds of Formula 1B, further G substituents may be present on the depicted phenyl or pyrimidinyl ring; due to the presence of "R," p is an integer from 0 to 3 in such compounds.

The ring "R" can be of varying sizes, can be substituted or unsubstituted, and can be comprised of carbon atoms and/or heteroatoms. R can comprise single bonds, double bonds, or any combination thereof. Certain non-limiting examples of rings include optionally substituted carbon-based rings, e.g., phenyl and cycloalkyl rings (e.g., cyclopentyl, cyclohexyl), optionally substituted N-containing rings (e.g., pyrrolidine, pyrroline, piperidine, piperazine rings, optionally substituted O-containing rings (e.g., furans, dioxolanes), and optionally substituted S-containing rings (e.g., thiophenes), as well as optionally substituted rings containing more than one heteroatom (e.g., oxazoles); resulting fused ring structures include, but are not limited to, optionally substituted fused rings including naphthalane, indenes, indolines/indoles, benzofurans, benzothiophines, benzooxazoles, benzothiazoles, benzoisoxazoles, benzimidazoles, quinoxalines, quinazolines, and the like.

Such compounds can find use, e.g., in treating or preventing diseases or disorders associated with dopamine binding, e.g., involving the central nervous system (CNS). In particular, compounds of Formula 1 (including 1A and 1B) provided above can bind as $D_4R$ ligands (binding such dopamine receptors and thereby acting upon the CNS). As such, the present disclosure provides a method for treating or delaying the progression of disorders that are alleviated by binding to the dopamine (e.g., $D_4R$) receptors in a patient, the method comprising administering a therapeutically effective amount of at least one compound of Formula 1 (or Formula 1A or 1B) to the patient. In some embodiments, the compounds show selectivity for subtype $D_4R$ binding over other dopamine receptor subtypes.

The disclosure may thus relate to the treatment of various conditions that may benefit from binding to the dopamine receptors. Although various such disorders and diseases are known, the compounds may be particularly applicable for treatment of cognitive disorders, treatment of addiction, e.g., cocaine addition, and treatment or prevention of drug addiction relapse (e.g., associated with cocaine addiction). In particular, the disclosure provides methods for treating cocaine addiction in animals, particularly humans and other mammals, and associated effects of these conditions.

The method of treatment generally includes administering a therapeutically effective amount of a compound of Formula 1 (or 1A or 1B), optionally in a pharmaceutical composition including one or more pharmaceutically acceptable carriers. The therapeutically effective amount is preferably sufficient to affect the $D_4R$ subtype receptor. The therapeutically effective amount is further preferably sufficient to cause some relief to the patient in the symptoms of the disorder for which the patient is being treated. A therapeutically effective dosage amount of any specific formulation will vary somewhat from compound to compound, patient to patient, and may depend upon factors such as the condition of the patient and the route of delivery. When administered conjointly with other pharmaceutically active agents, even less of the compound of Formula 1 (or 1A or 1B) may be therapeutically effective. Furthermore, the therapeutically effective amount may vary depending on the specific condition to be treated.

The compounds provided herein can be administered once or several times a day. Dosages can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

Compositions

While it is possible for the compounds of Formula 1 (or Formulas 1A or 1B) to be administered in the raw chemical form, it is generally preferred for the compounds to be delivered as a pharmaceutical formulation. Accordingly, there are provided by the present disclosure pharmaceutical compositions comprising at least one compound capable of functioning as an antagonist of a dopamine (e.g., the $D_4R$) receptor. As such, formulations provided herein comprise a compound of Formula 1 (or 1A or 1B), as described above, or a pharmaceutically acceptable ester, amide, salt, or solvate thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carriers) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). In some embodiments, the pharmaceutical compositions provided herein comprise one or more cyclodextrins.

Exemplary pharmaceutical excipients and/or additives suitable for use in the compositions according to the invention are listed in Remington: "The Science & Practice of Pharmacy," $21^{st}$ ed. Lippincott Williams & Wilkins (2006); in the Physician's Desk Reference, $64^{th}$ ed., Thomson PDR (2010); and in Handbook of Pharmaceutical Excipients, $6^{th}$ ed., Eds. Raymond C. Rowe et al., Pharmaceutical Press (2009), which are incorporated herein by reference.

Binders are generally used to facilitate cohesiveness of a tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and cross-linked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations provided herein may include short-term, rapid-onset, rapid-offset, controlled release, sustained release, delayed release, and pulsatile release formulations, providing the formulations achieve administration of a compound as described herein. See *Remington's Pharmaceutical Sciences* ($18^{th}$ ed.; Mack Publishing Company, Eaton, Pennsylvania, 1990), herein incorporated by reference in its entirety.

Pharmaceutical formulations according to the present disclosure are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent (e.g., a compound of Formula 1, 1A, or 1B as disclosed herein) or a pharmaceutically acceptable ester, amide, salt, or solvate thereof with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of such dosage forms are generally known in the art, and any such method would be suitable for the preparation of the respective dosage forms for use in delivery of the compounds according to the present disclosure.

A tablet containing a compound as provided herein may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present disclosure may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of Formulas 1, 1A, or 1B above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of the disclosed formulas into association with a carrier that constitutes one or more accessory ingredients. In general, the compositions are prepared by bringing a compound of the present disclosure into association with a liquid carrier to form a solution or a suspension, or alternatively, bringing a compound of the present disclosure into association with formulation components suitable for forming a solid, optionally a particulate product, and then, if warranted, shaping the product into a desired delivery form. Solid formulations provided herein, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula 1 (or 1A or 1B) in the formulation will vary depending the specific compound selected, dosage form, target patient population, and other considerations, and will be readily determined by one skilled in the art. The amount of the compound in the formulation will be that amount necessary to deliver a therapeutically effective amount of the compound to a patient in need thereof to achieve at least one of the therapeutic effects associated with the compounds of the disclosure. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Aspects of the present disclosure are more fully illustrated with reference to the following examples. Before describing several exemplary embodiments of the technology, it is to be understood that the technology is not limited to the details of construction or process steps set forth in the following description. The technology is capable of other embodiments and of being practiced or being carried out in various ways. The following examples are set forth to illustrate certain aspects of the present technology and are not to be construed as limiting thereof.

Experimentals

Synthesis:

4-chlorobutanoyl chloride (5.54 mL, 49.5 mmol) was added to a solution of 2-aminothiophenol (4.27 mL, 39.9 mmol) in toluene (150 mL) at 0° C. The reaction mixture was allowed to warm to room temperature and stirred 48 hours under a nitrogen atmosphere. After the reaction was complete, the solvent was removed in vacuo. The crude mixture was diluted with ethyl acetate (EtOAc) (200 mL) and washed with saturated aqueous $NaHCO_3$ (200 mL), and then extracted with EtOAc (3×200 mL) and washed with saturated brine (200 mL). The combined organic layer was dried over $Na_2SO_4$, filtered and concentrated. The product was purified by column chromatography (5-95% EtOAc: hexanes gradient) to give 2-(3-chloropropyl)benzo[d]thiazole as an off-white solid.

$K_2CO_3$ (4.57 g, 33.0 mmol) and NaI (50 mg) were added to a solution of the 2-(3-chloropropyl)benzo[d]thiazole (700 mg, 3.30 mmol) and substituted or unsubstituted piperidinyl or piperazinyl (3.97 mmol) in an anhydrous acetonitrile (12 mL) solution. The reaction mixture was stirred at reflux (80° C.) for 20 h, under nitrogen atmosphere. The reaction mixture was cooled to room temperature and the solvent was removed in vacuo. The residue was diluted with water (100 mL) and dichloromethane (DCM) (100 mL), and then extracted with DCM (3×100 mL) and washed with brine (100 mL). The combined organic layer was dried over $Na_2SO_4$, filtered and concentrated. The crude product was purified by column chromatography (98% CMA (chloroform/methanol/ammonium) gradient) to give the desired compounds.

An example scheme (Scheme 1) is provided below, showing the preparation of one compound within the scope of the present disclosure, namely, (2-(3-(4-(pyridin-2-yl)piperazin-1-yl)propyl)benzo[d]thiazole. Various other compounds were prepared according to similar methods with modification as needed of starting materials and reagents.
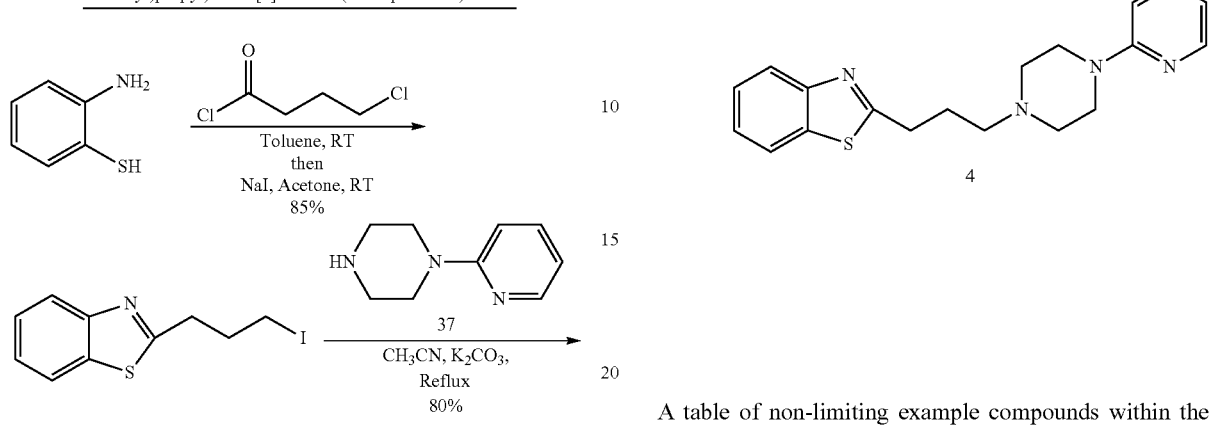
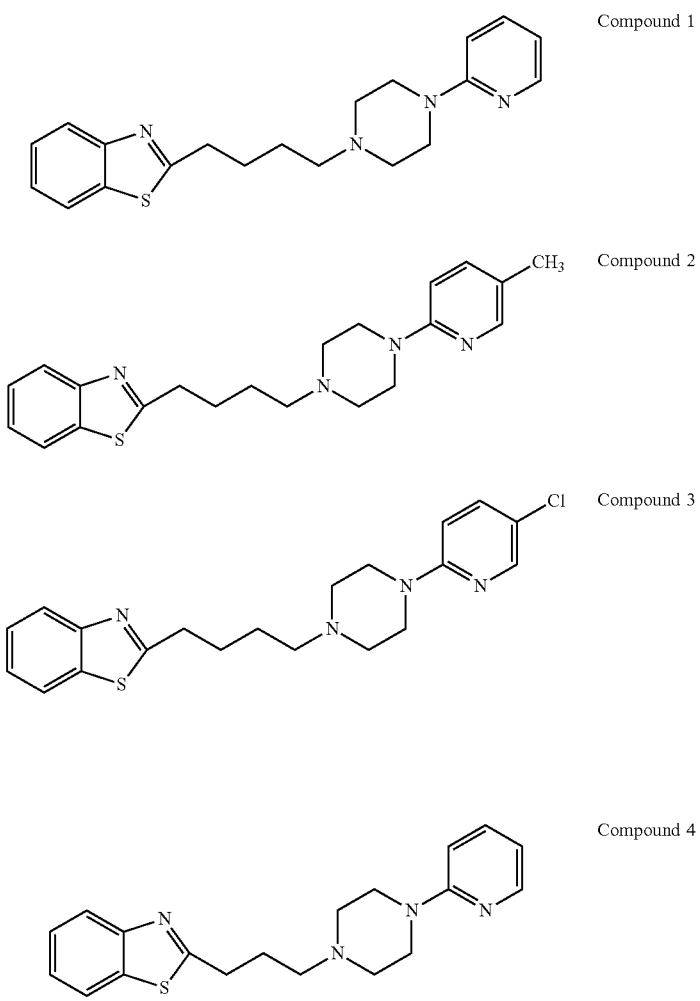
A table of non-limiting example compounds within the scope of the present disclosure is provided herein below.

TABLE 1-continued
Example Compounds of Formula 2
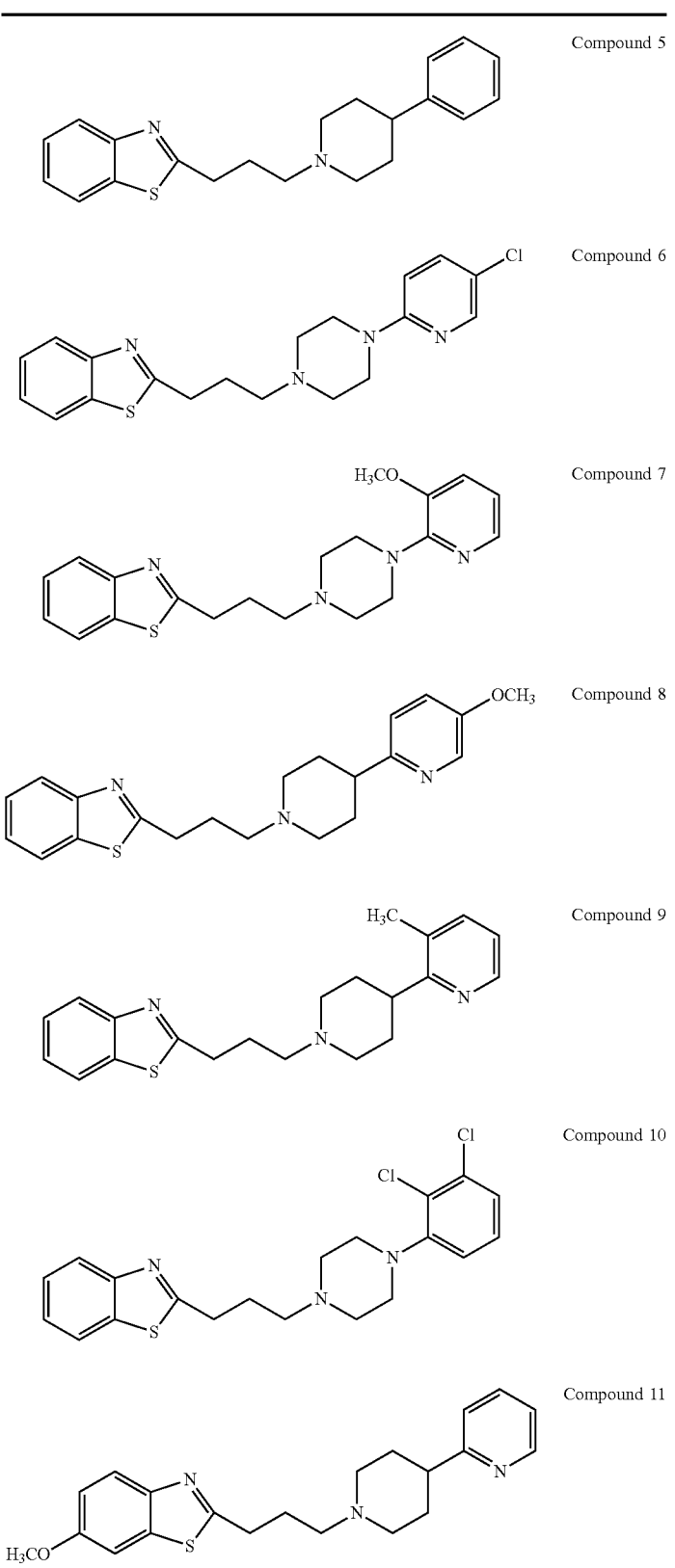
Compound 5
Compound 6
Compound 7
Compound 8
Compound 9
Compound 10
Compound 11

TABLE 1-continued
Example Compounds of Formula 2
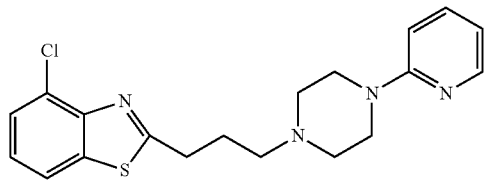 [SMILES: Clc1cccc2sc(CCCN3CCN(c4ccccn4)CC3)nc12]
Compound 12
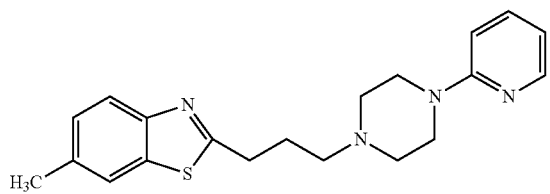 [SMILES: Cc1ccc2nc(CCCN3CCN(c4ccccn4)CC3)sc2c1]
Compound 13
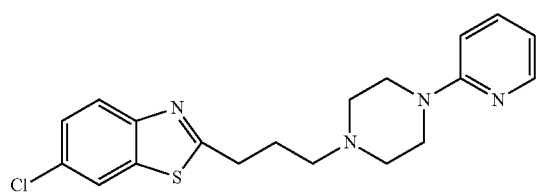 [SMILES: Clc1ccc2nc(CCCN3CCN(c4ccccn4)CC3)sc2c1]
Compound 14
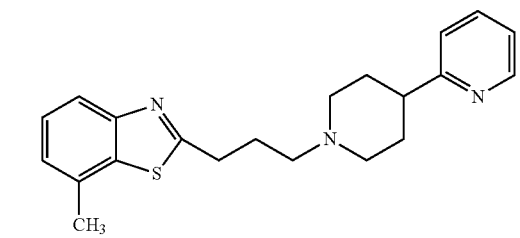
Compound 15
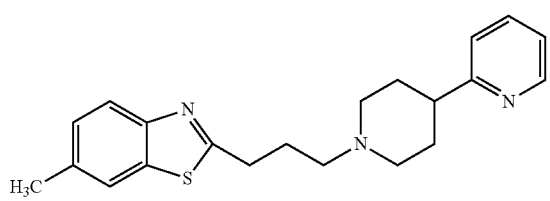 [SMILES: Cc1ccc2nc(CCCN3CCC(c4ccccn4)CC3)sc2c1]
Compound 16
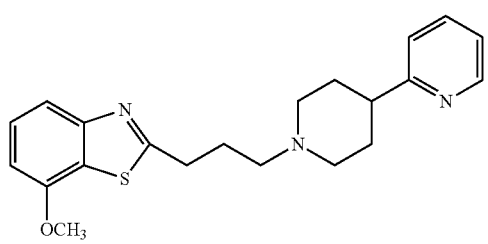 [SMILES: COc1cccc2nc(CCCN3CCC(c4ccccn4)CC3)sc12]
Compound 17
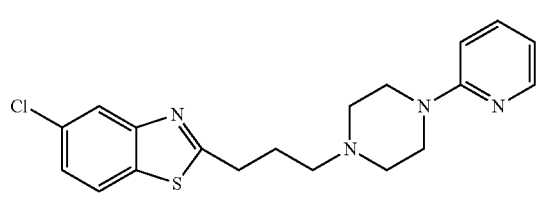 [SMILES: Clc1ccc2sc(CCCN3CCN(c4ccccn4)CC3)nc2c1]
Compound 18

TABLE 1-continued
Example Compounds of Formula 2
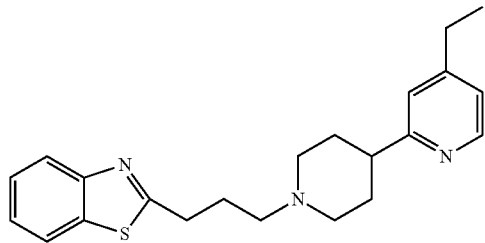 [SMILES: CCc1ccnc(C2CCN(CCCc3nc4ccccc4s3)CC2)c1]
Compound 19
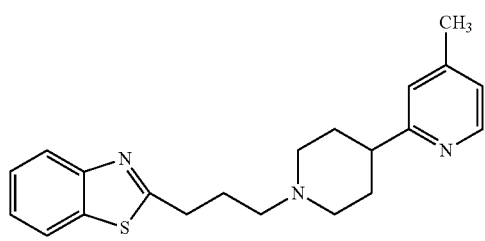 [SMILES: Cc1ccnc(C2CCN(CCCc3nc4ccccc4s3)CC2)c1]
Compound 20
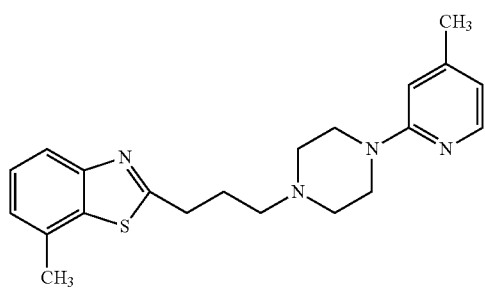 [SMILES: Cc1ccnc(N2CCN(CCCc3nc4cccc(C)c4s3)CC2)c1]
Compound 21
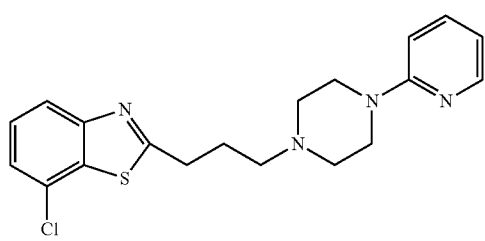 [SMILES: Clc1cccc2nc(CCCN3CCN(c4ccccn4)CC3)sc12]
Compound 22
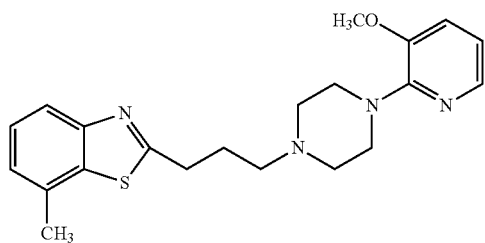
Compound 23
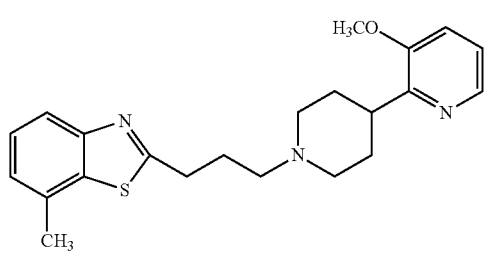 [SMILES: COc1cccnc1C1CCN(CCCc2nc3cccc(C)c3s2)CC1]
Compound 24

TABLE 1-continued
Example Compounds of Formula 2
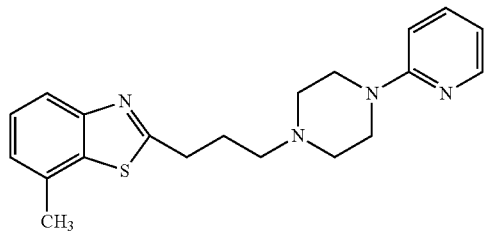 [SMILES: Cc1cccc2nc(CCCN3CCN(c4ccccn4)CC3)sc12]
Compound 25
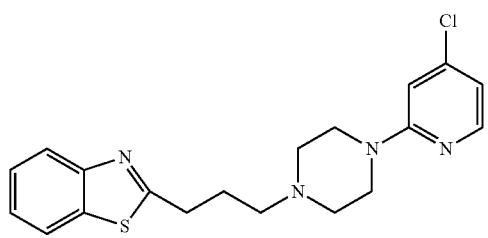 [SMILES: Clc1ccnc(N2CCN(CCCc3nc4ccccc4s3)CC2)c1]
Compound 26
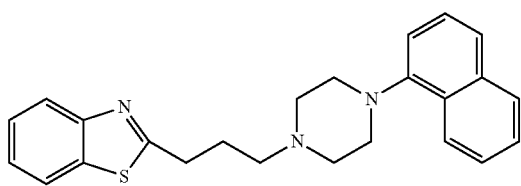 [SMILES: c1ccc2c(N3CCN(CCCc4nc5ccccc5s4)CC3)cccc2c1]
Compound 27
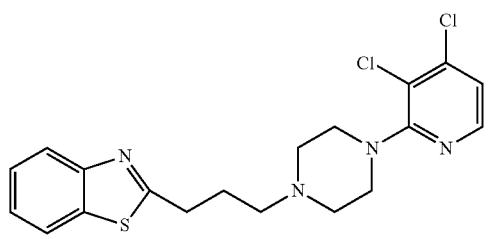 [SMILES: Clc1ccnc(N2CCN(CCCc3nc4ccccc4s3)CC2)c1Cl]
Compound 28
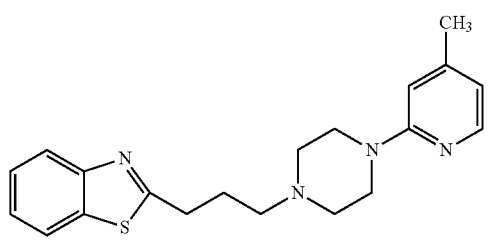 [SMILES: Cc1ccnc(N2CCN(CCCc3nc4ccccc4s3)CC2)c1]
Compound 29
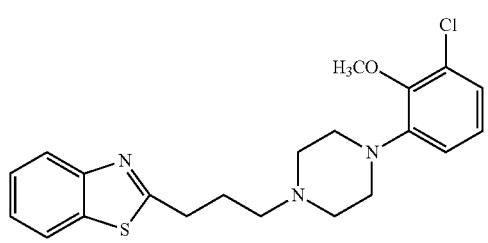 [SMILES: COc1c(Cl)cccc1N1CCN(CCCc2nc3ccccc3s2)CC1]
Compound 30

TABLE 1-continued
Example Compounds of Formula 2
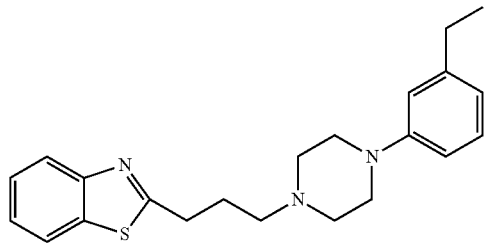 [SMILES: CCc1cccc(N2CCN(CCCc3nc4ccccc4s3)CC2)c1]
Compound 31
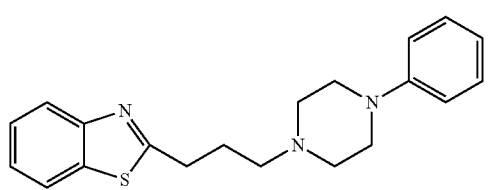 [SMILES: c1ccc(N2CCN(CCCc3nc4ccccc4s3)CC2)cc1]
Compound 32
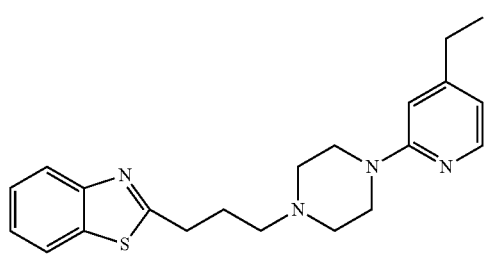 [SMILES: CCc1ccnc(N2CCN(CCCc3nc4ccccc4s3)CC2)c1]
Compound 33
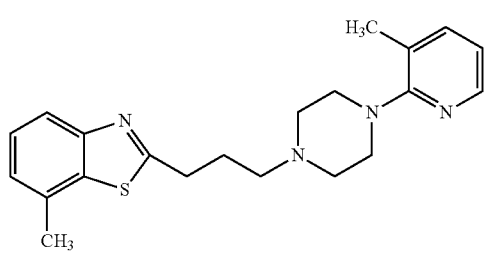
Compound 34
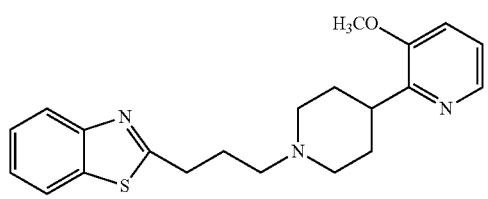 [SMILES: COc1cccnc1C1CCN(CCCc2nc3ccccc3s2)CC1]
Compound 35
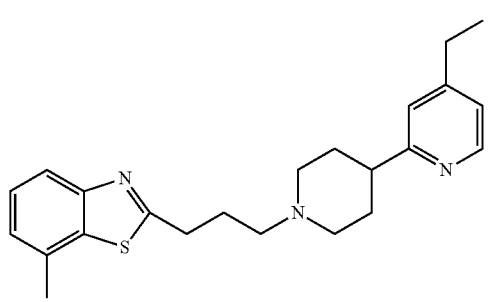 [SMILES: CCc1ccnc(C2CCN(CCCc3nc4cccc(C)c4s3)CC2)c1]
Compound 36

TABLE 1-continued

Example Compounds of Formula 2

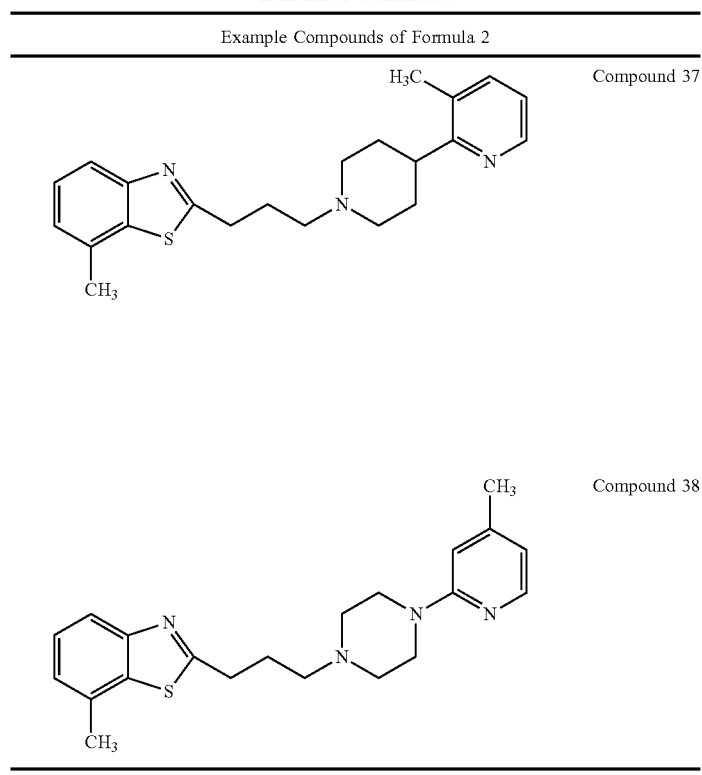

Compound 37

Compound 38

In Vitro and In Vivo Studies

In vitro binding affinities for various compounds within the scope of the present disclosure were determined using [$^3$H]N-methylspiperone radioligand binding in Human Embryonic Kidney (HEK293) cells expressing dopamine $D_2$-like receptors ($D_2R$, $D_3R$, $D_4R$). These binding studies were coupled with functional studies using radioligand binding β-arrestin recruitment and cAMP inhibition displacement assays. See Keck et al., J. Med. Chem. 2019, 62 (7), 3722-3740, which is incorporated herein by reference. The pharmacological analyses of compounds 1-4, using radioligand binding displacement assays, β-arrestin2 recruitment assays, cAMP inhibition assays are shown in Tables 2 and 3. Compound 4 clearly displayed $D_4R$ subtype-selective in binding assays with $D_4R$ affinity, $D_2$-like subtype selectivity (Ki≤2.21 nM and >100-fold vs. other $D_2$-like receptors; Table 2). Compound 4 displayed full antagonist activity as measured by Gαi/o-mediated signaling and β-arrestin2 recruitment (See Table 3).

Pharmacological Results and Discussion

The binding affinities of the compounds were evaluated by performing competition binding studies using [3H]N-methylspiperone radioligand binding in Human Embryonic Kidney (HEK293) cells expressing dopamine D2-like receptors (D2R, D3R, D4R). Binding data for the some of the full length substituted ligands are shown in Table 2. In addition, cLogP values and polar surface area (PSA) were calculated to provide measures of lipophilicity and predicted brain penetration respectively, for the full-length compounds. The majority of analogues demonstrated binding affinities in the low nanomolar range for D4R. In the 1-(pyridin-2-yl)piperazine based series (compounds 1-3) with butyl linker chain, both compounds 1 and 3 showed high binding affinities for D4R=9.85 and 4.85 nM, respectively). Substituents on the pyridinyl moiety of compound 1 could be accommodated as shown by the methoxy analog 7 with high binding affinity (D4R=1.14 nM) with selectivity of D4R (≥251) over D2R and D3R. Other chain lengths could be accommodated as shown by replacing the butyl linker chain like compound 1 with propyl linker chain like compound 4 gave an improved nanomolar binding affinity (D4R=2.21 nM) and selectivity ≥520 were increased over D2R and D3R. When the piperazine ring was also replaced with other substituted piperidinyl ring system, such as 5-methoxy-2-(piperidin-4-yl)pyridine (8), 3-methyl-2-(piperidin-4-yl)pyridine (9). In most of cases, D4R binding affinities (D4R=22.0 and 26.0 nM respectively) were retained or reduced, an improvements in D4R over D2R selectivity. But compound 19, D4R binding affinity (D4R=5.89 nM) was retained including an improvement in D4R over D2R and D3R selectivity.

In the more highly substituted 2-(3-(4-(pyridin-2-yl)piperidin-1-yl) propyl)benzo[d]thiazole-based series (compound 15), the 7-methyl substitution on compound 15 exhibited high binding affinity profile than its analogue 6-methyl substitution on compound 16 and the greatest D4R versus D2R and D3R binding selectivity, (>15907 fold). Reduced in selectivity of compound 14 was observed with 6-chloro substitution on the pyridinyl moiety. Most of the butyl and propyl linking chain compounds exhibited cLogP values lower than ≤5 value. None of the compounds demonstrated higher binding affinity for D2R and D3R. The substituted full length molecules based on both 2-(piperidin-4-yl)pyridine and 1-(pyridin-2-yl)piperazine moieties with propyl linking chain showed high D4R binding affinities and selectivities over D2R and D3R.

TABLE 2

Human dopamine $D_2$-like receptor binding data for selected compounds[a]

| Cmpd | cLogP | PSA | $K_i$ (nM) ± SEM $D_2R$ | $K_i$ (nM) ± SEM $D_3R$ | $K_i$ (nM) ± SEM $D_4R$ | Selectivity $D_2R/D_4R$ | Selectivity $D_3R/D_4R$ |
|---|---|---|---|---|---|---|---|
| 1 | 4.15 | 31.2 | 408 ± 20.6 | 58.5 ± 1.16 | 9.85 ± 2.01 | 41 | 6 |
| 2 | 4.53 | 31.2 | 1050 ± 165 | 205 ± 2.70 | 21.2 ± 1.37 | 50 | 10 |
| 3 | 4.83 | 31.2 | 830 ± 158 | 104 ± 3.78 | 4.85 ± 0.57 | 171 | 21 |
| 4 | 3.63 | 31.2 | 2930 ± 169 | 1150 ± 194 | 2.21 ± 0.01 | 1326 | 520 |
| 7 | 3.93 | 40.43 | 777 ± 12.5 | 288 ± 194 | 1.14 ± 0.21 | 679 | 251 |
| 8 | 3.96 | 37.19 | 17400 ± 8490 | 4860 ± 3870 | 22.0 ± 1.04 | 788 | 221 |
| 9 | 3.99 | 27.96 | 13300 ± 9000 | 773 ± 213 | 26.0 ± 13.4 | 510 | 30 |
| 15 | 4.21 | 27.96 | 18028 ± 15210 | 37124 ± 30281 | 1.13 ± 0.27 | 15907 | 32756 |
| 16 | 4.21 | 27.96 | 6894 ± 4680 | 11800 ± 9500 | 54.7 ± 36.7 | 126 | 215 |
| 19 | 4.56 | 27.96 | 12300 ± 7670 | 16700 ± 13300 | 5.89 ± 3.95 | 2082 | 2838 |

[a] $K_i$ values determined by competitive inhibition of [$^3$H]N-methylspiperone binding in membranes harvested from HEK 293 cells stably expressing $hD_2R$, $hD_3R$, or $hD_4R$. $K_i$ values presented as means ± SEM.
n = 3-6 dose-response curves.

TABLE 3

$D_4R$ efficacy of Compound 4 as measured via modulation of β-anestin2 recruitment and cAMP accumulation.[a]

| Compound | β-arr $E_{max}$ | β-arr $EC_{50}$ (nM) | β-arr Ant. % | β-arr $IC_{50}$ (nM) | cAMP $E_{max}$ % | cAMP $EC_{50}$ (nM) | cAMP Ant. % | cAMP $IC_{50}$ (nM) |
|---|---|---|---|---|---|---|---|---|
| 4 | Inactive | Inactive | 98 ± 2 | 48.8 ± 14.0 | Inactive | Inactive | 95 ± 5 | 18.7 ± 1.3 |

[b] Values determined by nonlinear regression of individual experiments run in triplicate.
All $EC_{50}$, $IC_{50}$, and $E_{max}$ values are presented as means ± SEM; n = 3-4.
Inactive indicates no measurable activity in indicated assay.

Brain penetrance of compound 4, and brain-penetrant ligand buspirone were evaluated in silico using central nervous system multiparameter optimization (CNS MPO) tools, with calculated CNS MPO score of 4.5 and 5.8, respectively; scores >4 correlate with high CNS penetrance. See Wager et al., ACS Chem. Neuroscience, 2016, 7(6), 767-75, which is incorporated herein by reference in its entirety. Compound 4 was tested in Caco-2 membrane permeability tests (Eurofins Panlabs, St. Charles, MO): apical-to-basolateral (A-B) permeability of compound 4 was $27 \times 10^{-6}$ cm/s, comparable to control propranolol ($24 \times 10^{-6}$ cm/s) and for known brain-penetrant CNS ligand buspirone ($25 \times 10^{-6}$ cm/s).

Microsomal Metabolism Studies: Rat, and Human Liver Microsomes

Figure 1B:
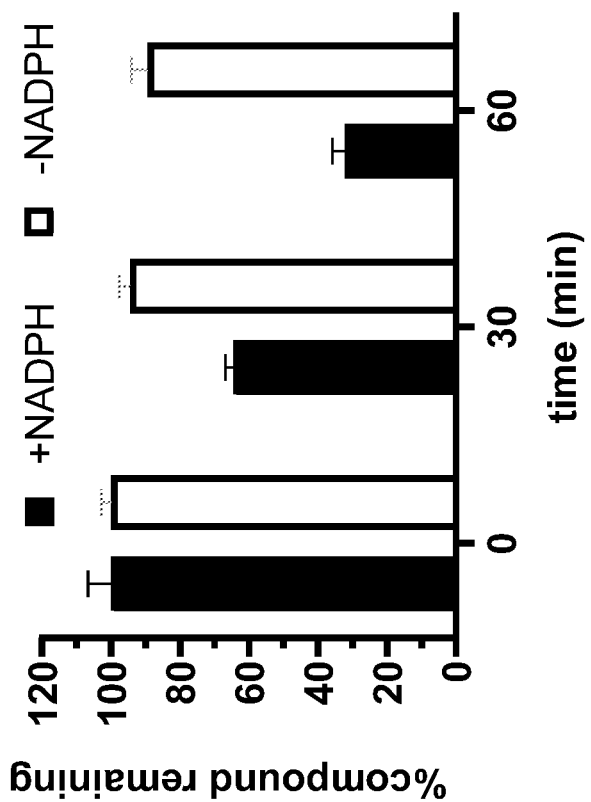

Compound 4 was evaluated for Phase I metabolic stability using rat and human liver microsomes. See Battiti et al., J. Med. Chem. 2019, 62(13), 6287-6314, which is incorporated herein by reference in its entirety. Incubation of compound 4 with rat microsomes in the presence of NADPH resulted in time-dependent degradation with ~33% remaining after 1-hr (see FIG. 1A). In human liver microsomes, compound 4 showed modest stability with ~60% remaining after a 1-hr incubation (see FIG. 1B). These results indicate that compound 4 has decent liver metabolic stability in humans and relatively lower stability in rat liver. Compound 4 was further evaluated for in vivo pharmacokinetics in rats.

Pharmacokinetic Assessment of Compound 4 in Rats

Figures 2A, 2B:
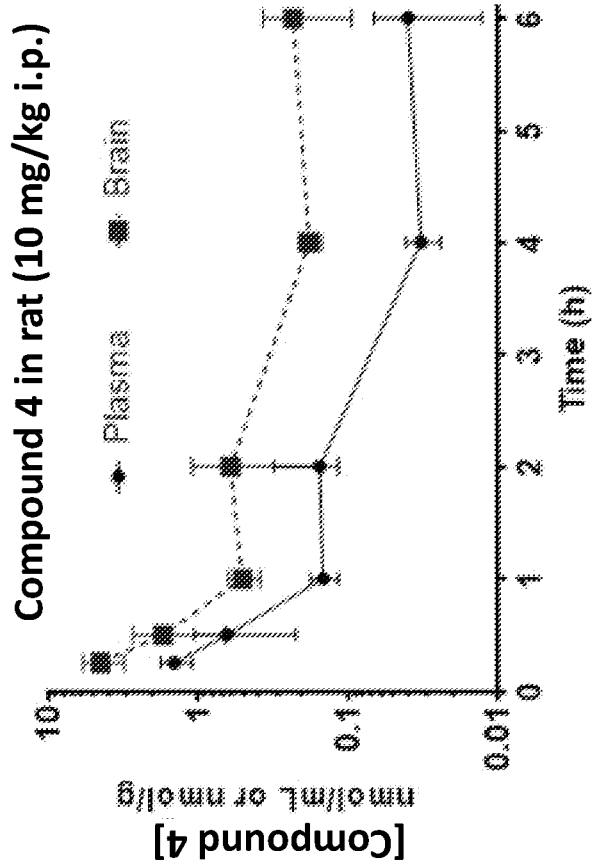
FIG. 2A and FIG. 2B provide a time-dependent in vivo pharmacokinetic analysis of one example compound of an embodiment of the disclosure in sprague dawley (SD) rats following interperitonieal (i.p.) administration of 10 mg/kg of the compound (2A) (data expressed as mean±SEM, n=3) and pharmacokinetics parameters of the compound in rats (2B)

Evaluation of in vivo pharmacokinetic profile of compound 4 in rats was performed. Rats were dosed intraperitoneally (10 mg/kg) and plasma and brain levels of compound 4 were measured from 0 to 6 h post dose. The results from the pharmacokinetic analysis are shown in FIGS. 2A and 2B.

Following intra-peritoneal administration, compound 4 demonstrated good exposures in both plasma and brain with AUC0-t of 1.05 nmol*h/ml and 3.67 nmol*h/g respectively. Moreover, compound 4 showed a remarkable brain penetration index (AUCbrain/plasma ratio) of 3.5 with an apparent half-life of ~1h (t1/2). The detailed pharmacokinetic parameters of the compound 4 are provided in FIG. 2B.

In Vivo Studies

Figure 3:
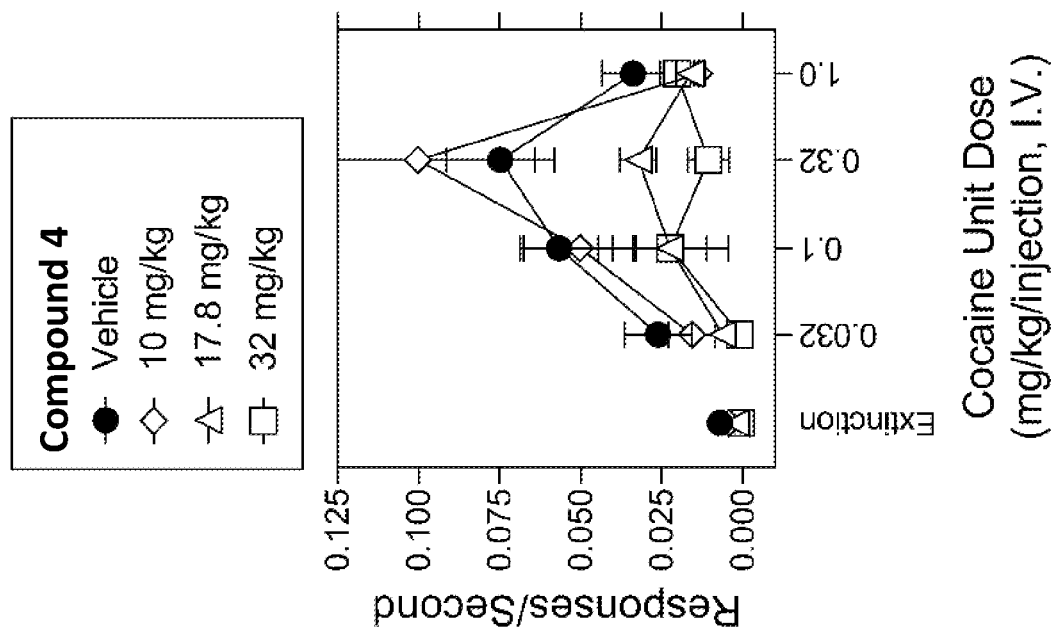
FIG. 3 is a graph of data demonstrating the effect of one example compound of an embodiment of the disclosure on cocaine self-administration, where the abscissa provides the extinction (no injection) and cocaine dose in mg/kg/injection (i.v., log scale) and the ordinate provides the responses per second), and where each point represents the mean±SEM (n=4 rats/sex)

Using a multi-component, drug self-administration assay under a fixed ratio 5-responsee schedule of reinforcement in Sprague-Dawley rats (n=8), the dopamine D4R selective antagonist compound 4 (i.p.) dose-dependently shifted downward a dose-effect function of cocaine self-administration (See FIG. 3, in which compound 4 was administered i.p. 5 minutes before sessions; the vehicle was sterile water containing 5% Tween® 80 and 5% propylene glycol). 17.8 and 32 mg/kg compound of compound 4 significantly decreased the maximum rates of responding maintained by injections of cocaine (0.32 mg/kg/injection, i.v.).

Figure 4B:
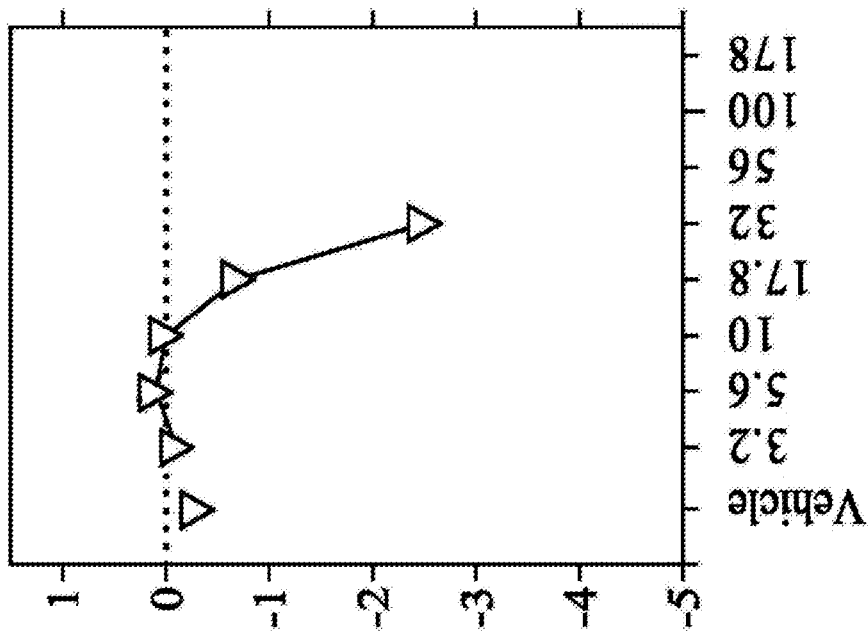
FIGS. 4A and 4B are graphs of data demonstrating the effect of one example compound of an embodiment of the disclosure on food-maintained responding and rectal temperature, where the abscissae provide cumulative dose in mg/kg (i.p., log scale), and the ordinates are control response rate (4A) and change in temperature (4B), and where each point represents the mean±SEM (n=4 rats/sex).
Figure 4A:
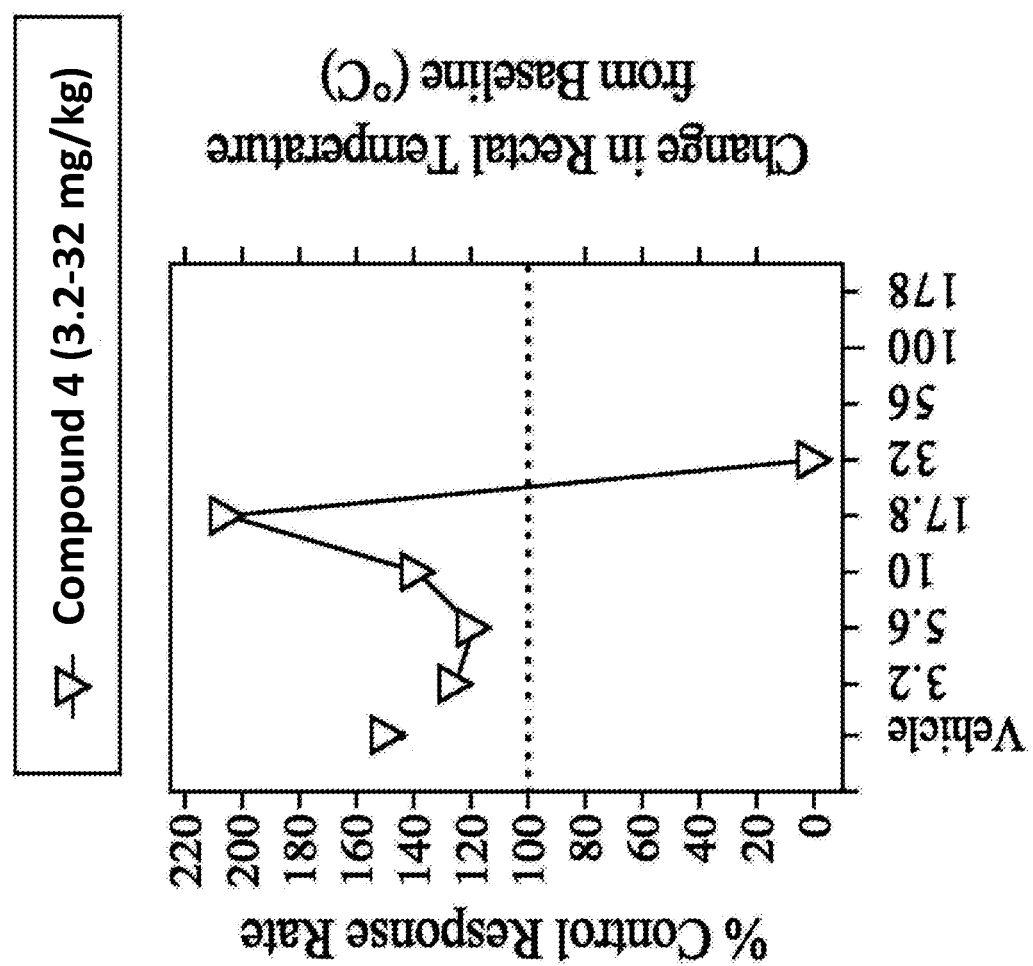

The antagonizing effects of compound 4 could be due to non-specific behavioral disruption. Thus, follow-up studies in rats were conducted to assess the specificity of effects of compound 4 (See FIG. 4). No dose of cumulative dosing of compound 4 except 32 mg/kg significantly decreased lever-responding maintained by food pellets, non-drug reinforcer (n=8), or rectal temperature (n=8). Thus, 32 mg/kg might have produced non-specific negative impact on behavior and physiology (e.g., off-target effects at dopamine D2Rs). However, compound 4 at 17.8 mg/kg antagonized the reinforcing effects of cocaine.

Follow-up studies showed that compound 4 did not disrupt food-maintained responding below doses of 32 mg/kg, at which point effects are likely mediated by off-target effects at $D_2R$ as shown by an associated hypothermic response. See FIG. 4, providing a graph of effects of $D_4R$ antagonist compound 4 on food-maintained responding and body temperature, with mean±SEM response rate and change in body temperature following cumulative dosing procedure. The vehicle was sterile water containing 5% Tween® 80 and 5% propylene glycol. Compound 4 did not disrupt food-maintained responding or produce non-specific ($D_2R$-mediated) hypothermic responses below 32 mg/kg in male Sprague-Dawley rats (n=6). See Collins et al., *Psychopharmacology* 2007, 193(2), 159-70, which is incorporated herein by reference in its entirety.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the pending claims Although specific terms are employed herein, they are used in a generic and descriptive sense only and not for purposes of limitation.

What is claimed is:
1. A compound of Formula 1:

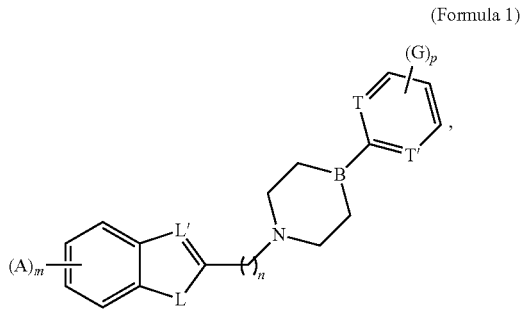

(Formula 1)

wherein:
A is selected from halogen, optionally substituted C1-6 alkyl, C1-6 alkenyl, $OR_1$, and $N(R_1)_2$;
m is an integer from 0-4 wherein, when more than one A is present, each A may be the same or different;
$R_1$ is selected from H and C1-6 alkyl;
L is S and L' is N;
n is an integer from 2 to 4;
B is N or C;
T is N and T' is C; and
G is selected from halogen, C1-6 alkyl, C1-6 alkenyl, $OR_1$, and $N(R_1)_2$, wherein, when T' is C and a substituent is present on T', it may, together with a substituent on an adjacent carbon atom, form an optionally substituted ring; and
p is an integer from 0-5 wherein, when more than one G is present, each G may be the same or different.

2. The compound of claim 1, wherein n is 3.
3. The compound of claim 1, wherein B is N.
4. The compound of claim 1, wherein B is C.
5. The compound of claim 1, wherein m is 1 or 2.
6. The compound of claim 1, wherein at least one A is present, and wherein the at least one A is selected from halogen, C1-6 alkyl, and $OR_1$.

7. The compound of claim 6, wherein the at least one A is selected from chloro, methyl, and methoxy.
8. The compound of claim 1, wherein m is 0.
9. The compound of claim 1, wherein p is 1 or 2.
10. The compound of claim 1, wherein at least one G is present, and wherein the at least one G is selected from halogen, C1-6 alkyl, and $OR_1$.
11. The compound of claim 10, wherein the at least one G is selected from chloro, methyl, ethyl, n-propyl, and methoxy.
12. The compound of claim 1, wherein a first G is present on T' and a second G is present on the adjacent carbon, wherein the first and second G together form a phenyl ring.
13. The compound of claim 1, wherein p is 0.
14. A compound, selected from the group consisting of:

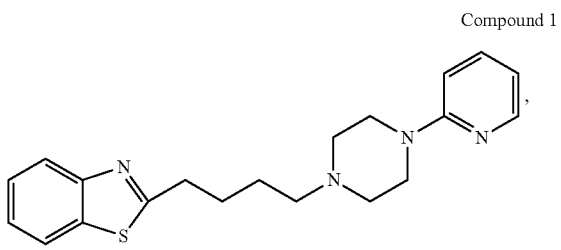

Compound 1

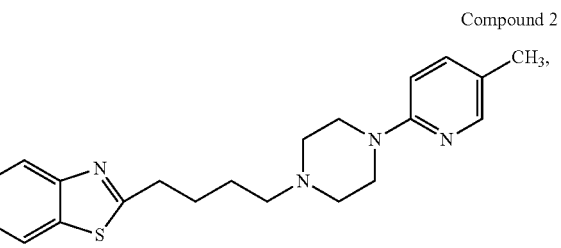

Compound 2

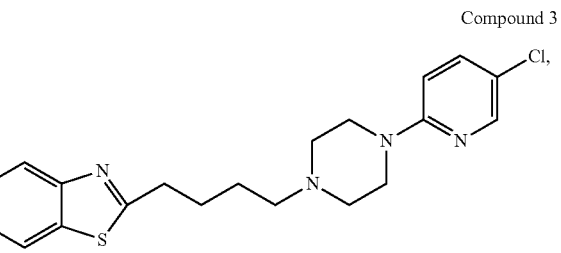

Compound 3

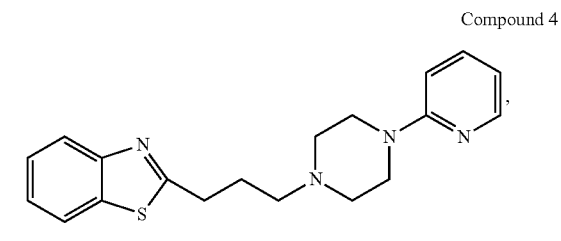

Compound 4

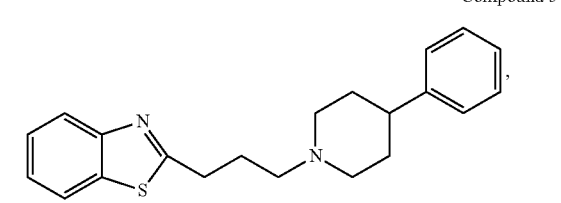

Compound 5

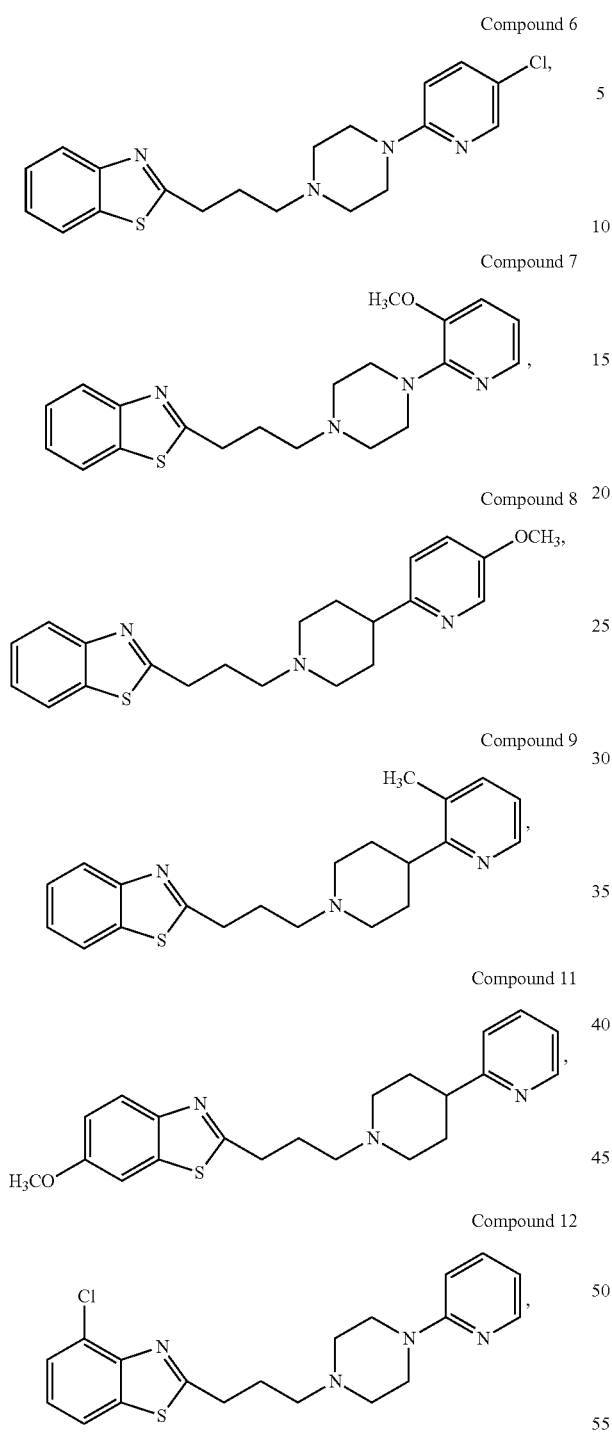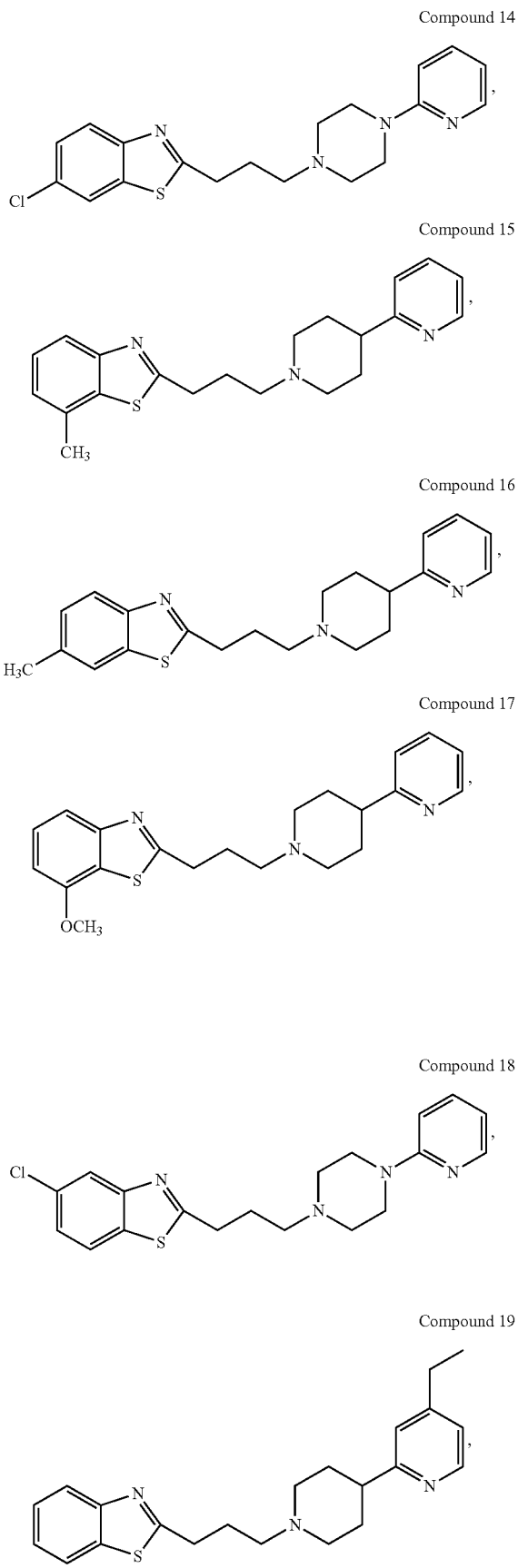

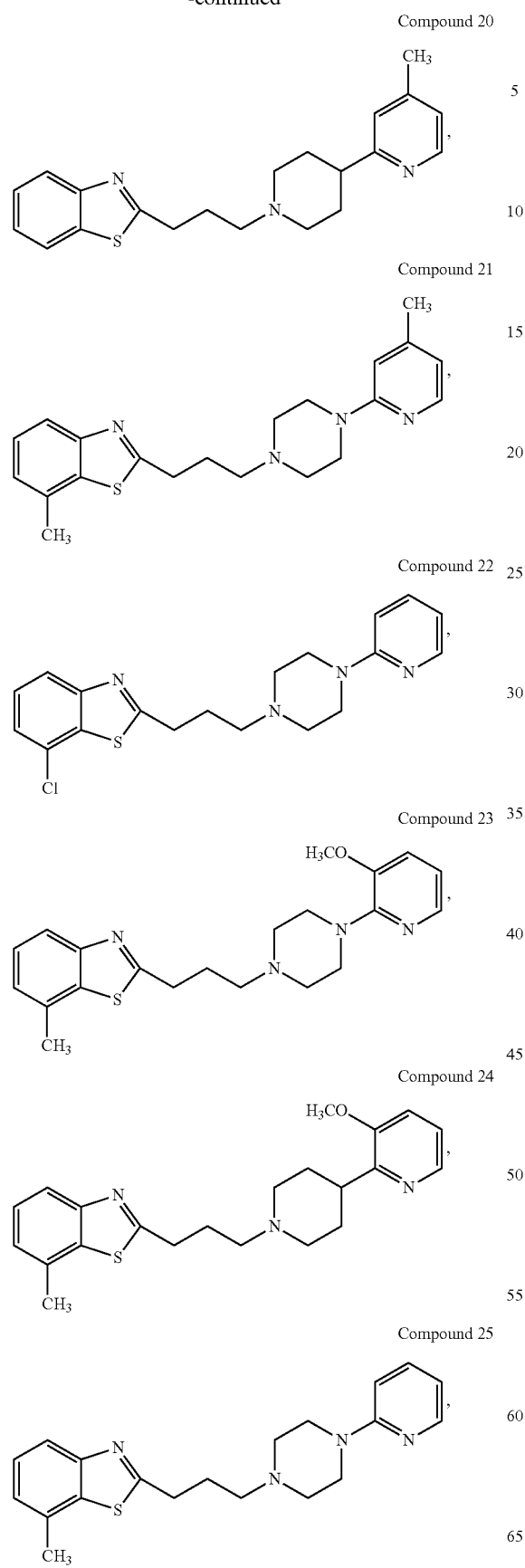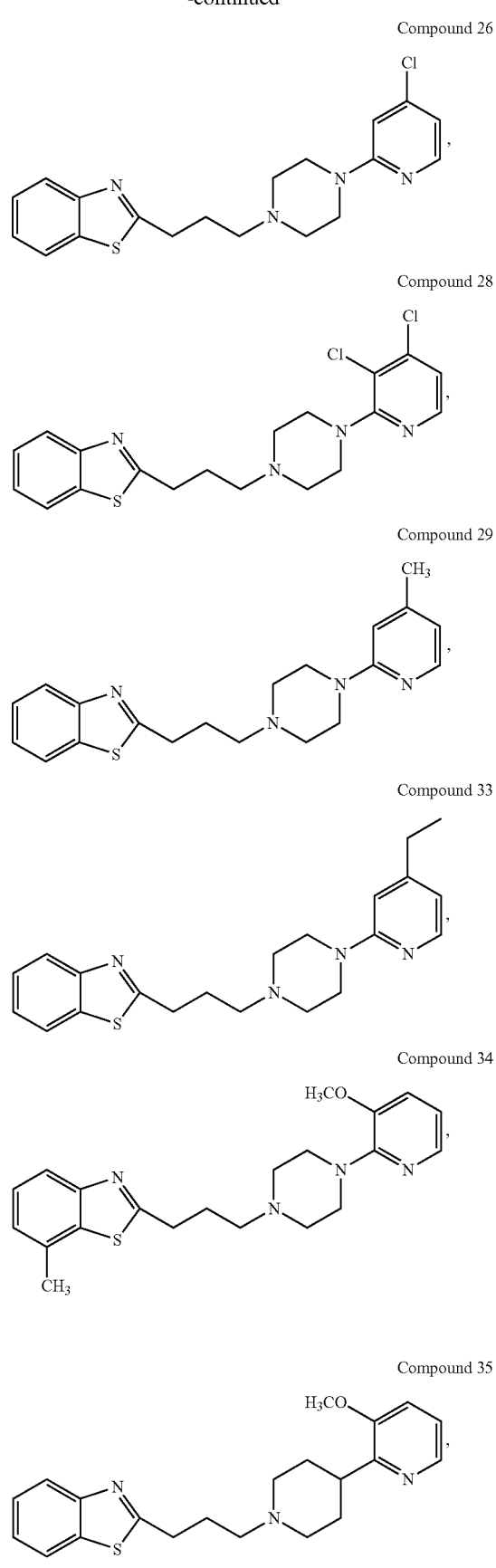

-continued

Compound 36

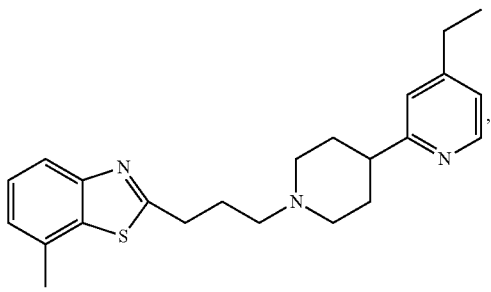

Compound 37

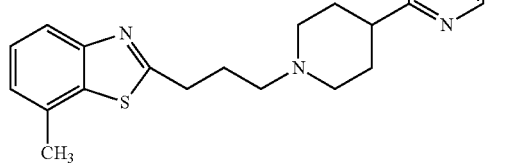
and

Compound 38

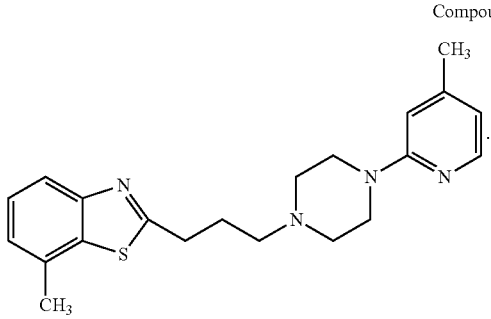

15. A pharmaceutical composition comprising the compound of claim 1 and one or more pharmaceutically acceptable carriers.

16. A method for treating a disease or disorder of the central nervous system, comprising administering a therapeutically effective amount of the compound of claim 1.

17. The method of claim 16, wherein the disease or disorder is cocaine addiction.

18. A pharmaceutical composition comprising the compound of claim 14 and one or more pharmaceutically acceptable carriers.

19. A method for treating a disease or disorder of the central nervous system, comprising administering a therapeutically effective amount of the compound of claim 14.

20. The method of claim 19, wherein the disease or disorder is cocaine addiction.

21. A compound of Formula 1:

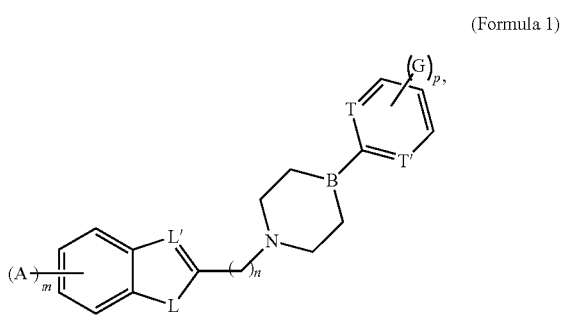

(Formula 1)

wherein:
A is selected from halogen, optionally substituted C1-6 alkyl, C1-6 alkenyl, $OR_1$, and $N(R_1)_2$;

m is an integer from 0-4 wherein, when more than one A is present, each A may be the same or different;

$R_1$ selected from H and C1-6 alkyl;

L is S and L' is N;

n is an integer from 2 to 4;

B is N;

T is N and T' is C; and

G is selected from halogen, C1-6 alkyl, C1-6 alkenyl, $OR_1$, and $N(R_1)_2$, wherein, when T' is C and a substituent is present on T', it may, together with a substituent on an adjacent carbon atom, form an optionally substituted ring; and p is an integer from 0-5 wherein, when more than one G is present, each G may be the same or different.

22. The compound of claim 1, which is

Compound 4

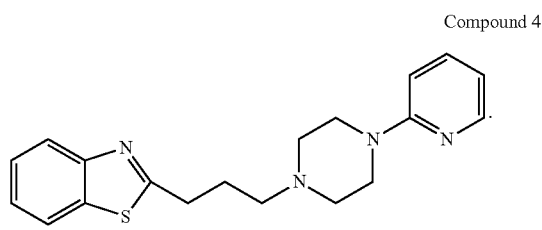 [SMILES: c1ccc(N2CCN(CCCc3nc4ccccc4s3)CC2)nc1]

* * * * *